United States Patent [19]

Schuetz et al.

[11] Patent Number: 5,166,399

[45] Date of Patent: Nov. 24, 1992

[54] SUBSTITUTED OXIME ETHERS AND FUNGICIDES WHICH CONTAIN THESE COMPOUNDS

[75] Inventors: Franz Schuetz, Ludwigshafen; Hubert Sauter, Mannheim; Albrecht Harreus, Ludwigshafen; Wolfgang Rohr, Wachenheim; Michael Hepp, Ladenburg; Siegbert Brand, Weinheim; Bernd Wenderoth, Lampertheim; Gisela Horenz, Neustadt; Eberhard Ammermann, Ludwigshafen, all of Fed. Rep. of Germany

[73] Assignee: BASF Aktiengesellschaft, Ludwigshafen, Fed. Rep. of Germany

[21] Appl. No.: 484,544

[22] Filed: Feb. 26, 1990

[30] Foreign Application Priority Data

Mar. 9, 1989 [DE] Fed. Rep. of Germany ....... 3907629
Nov. 10, 1989 [DE] Fed. Rep. of Germany ....... 3937457

[51] Int. Cl.$^5$ ................ C07C 229/36; C07C 229/34; C07C 229/32
[52] U.S. Cl. ................... 560/35; 546/335; 549/77
[58] Field of Search ............ 560/35; 546/335; 549/77; 514/357, 438, 539

[56] References Cited

U.S. PATENT DOCUMENTS

| | | | |
|---|---|---|---|
| 4,709,078 | 11/1987 | Schirmer et al. | 560/60 |
| 4,723,034 | 2/1988 | Schirmer et al. | 560/60 |
| 4,782,177 | 11/1988 | Schirmer et al. | 560/60 |
| 4,822,908 | 4/1989 | Karbach et al. | 560/60 |
| 4,829,085 | 5/1989 | Wenderoth | 514/522 |
| 4,870,075 | 9/1989 | Clough et al. | 514/255 |

FOREIGN PATENT DOCUMENTS

| | | |
|---|---|---|
| 0242081 | 10/1987 | European Pat. Off. . |
| 0254426 | 1/1988 | European Pat. Off. . |
| 0278595 | 8/1988 | European Pat. Off. . |
| 0307103 | 3/1989 | European Pat. Off. . |
| 2193495 | 2/1988 | United Kingdom . |

Primary Examiner—Jose G. Dees
Assistant Examiner—B. Frazier
Attorney, Agent, or Firm—Oblon, Spivak, McClelland, Maier & Neustadt

[57] ABSTRACT

Substituted oxime ethers of the general formula

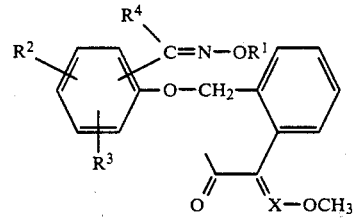

where $R^1$ is alkyl, alkenyl, alkynyl, haloalkyl, haloalkenyl, alkoxyalkyl, cycloalkyl, cycloalkylalkyl, cyanoalkyl, alkoxycarbonylalkyl, arylalkyl, heteroarylalkyl, arylalkenyl or aryloxyalkyl, the aromatic or heteroaromatic ring being substituted or unsubstituted, $R^2$ and $R^3$ are hydrogen, alkyl, haloalkyl, alkoxy, haloalkoxy, halogen, cyano or nitro, $R^4$ is hydrogen, alkyl or aryl, the aromatic ring being substituted or unsubstituted, and X is CH or N, and fungicides containing these compounds.

6 Claims, No Drawings

SUBSTITUTED OXIME ETHERS AND FUNGICIDES WHICH CONTAIN THESE COMPOUNDS

The present invention relates to novel substituted oxime ethers and fungicides which contain these compounds.

The use of oxime ethers such as, for example, methyl 2-phenoxymethylphenylglyoxylate O-methyloxime as fungicides has been disclosed (EP 253,213). However, their fungicidal action is often inadequate.

We have now found that substituted oxime ethers of the general formula I

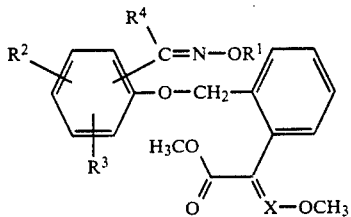

where $R^1$ is $C_1$-$C_6$-alkyl, $C_3$-$C_6$-alkenyl, $C_3$-$C_1$-alkynyl, $C_1$-$C_6$-haloalkyl, $C_3$-$C_6$-haloalkenyl, $C_1$-$C_4$-alkoxy-$C_1$-$C_6$-alkyl, $C_3$-$C_6$-cycloalkyl, $C_3$-$C_6$-cycloalkyl-$C_1$-$C_4$-alkyl, cyano-$C_1$-$C_6$-alkyl, $C_1$-$C_6$-alkoxycarbonyl-$C_1$-$C_6$-alkyl, aryl-$C_1$-$C_6$-alkyl, heteroaryl-$C_1$-$C_6$-alkyl, aryl-$C_3$-$C_6$-alkenyl or aryloxy-$C_1$-$C_6$-alkyl, it being possible for the aromatic or heteroaromatic ring to be substituted by one or more of the following: $C_1$-$C_4$-alkyl, $C_1$-$C_2$-haloalkyl, $C_3$-$C_6$-cycloalkyl, $C_1$-$C_4$-alkoxy, $C_1$-$C_2$-haloalkoxy, halogen, aryl or aryloxy, $R^2$ and $R^3$ are identical or different and are hydrogen, $C_1$-$C_4$-alkyl, $C_1$-$C_2$-haloalkyl, $C_1$-$C_4$-alkoxy, $C_1$-$C_2$-haloalkoxy, halogen, cyano or nitro, $R^4$ is hydrogen, $C_1$-$C_6$-alkyl or aryl, it being possible for the aromatic ring to be substituted by one or more of the following: $C_1$-$C_4$-alkyl, $C_1$-$C_2$-haloalkyl, $C_1$-$C_4$-alkoxy, $C_1$-$C_2$-haloalkoxy, halogen, cyano or nitro, and X is CH or N, have an excellent fungicidal action which is better than that of the known oxime ethers.

Examples of possible meanings of the radicals in the general formula are:

$R^1$ $C_1$-$C_6$-alkyl ($C_1$-$C_4$-alkyl) (e.g. methyl, ethyl, n- or isopropyl, n-, iso-, sec- or tert-butyl, n-, iso-, sec-, tert- or neo-pentyl hexyl), $C_3$-$C_6$-alkenyl (e.g. allyl, 2-butenyl, 3-buteryl, 1-methyl-2-propenyl, 2-methyl-2-propenyl), $C_3$-$C_4$-alkynyl (e.g. propargyl, 2-butynyl), $C_1$-$C_6$-haloalkyl (e.g. 2-fluoroethyl), $C_3$-$C_6$-haloalkenyl (e.g. 3-chloroallyl), $C_1$-$C_4$-alkoxy-$C_1$-$C_6$-alkyl (e.g. 2-methoxyethyl, 3-ethoxypropyl), $C_3$-$C_6$-cycloalkyl (e.g. cyclopropyl, cyclobutyl, cyclopentyl, cyclohexyl), $C_3$-$C_6$-cycloalkyl-$C_1$-$C_4$-alkyl (e.g. cyclopropylmethyl, cyclohexylmethyl), cyano-$C_1$-$C_6$-alkyl (e.g. cyanomethyl, 3-cyanopropyl), $C_1$-$C_6$-alkoxy-carbonyl-$C_1$-$C_3$-alkyl (e.g. ethoxycarbonylmethyl, tert-butoxycarbonylmethyl, tert-butoxycarbonylpropyl), aryl-(phenyl)-$C_1$-$C_6$-alkyl (e.g. benzyl, 2-phenylethyl, 3-phenylpropyl, 4-phenylbutyl), heteroaryl-(pyridyl, thienyl)-$C_1$-$C_6$-alkyl 3-pyridylmethyl, 2-thienylmethyl), aryl-(phenyl)-$C_3$-$C_6$-alkenyl (e.g.4-phenyl-2-butenyl, 4-phenyl-3-butenyl), aryloxy-(phenoxy)-$C_1$-$C_6$-alkyl (e.g. phenoxymethyl, phenoxyethyl, phenoxypropyl, phenoxybutyl, naphthoxymethyl, naphthoxyethyl), it being possible for the aromatic (phenyl) or heteroaromatic (pyridyl, thienyl) ring to be substituted by one or more, e.g. 1 to 5, in particular 1 to 3, of the following:

$C_1$-$C_4$-alkyl (e.g. methyl, ethyl, propyl, butyl), $C_1$-$C_2$-haloalkyl (e.g. trifluoromethyl, trichloromethyl), $C_3$-$C_6$-cycloalkyl (e.g. cyclopropyl, cyclobutyl, cyclopentyl, cyclohexyl), $C_1$-$C_4$-alkoxy (e.g. methoxy, ethoxy, propoxy, butoxy), $C_1$-$C_2$-haloalkoxy (e.g. trifluoromethoxy), halogen (e.g. fluorine, chlorine, bromine), aryl (e.g. phenyl), aryloxy (e.g. phenoxy), $R^2$ and $R^3$, which can be identical or different, hydrogen, $C_1$-$C_4$-alkyl (e.g. methyl, ethyl, n- or isopropyl, butyl), $C_1$-$C_2$-haloalkyl (e.g. trifluoromethyl, trichloromethyl), $C_1$-$C_4$-alkoxy (e.g. methoxy, ethoxy, n- or iso-propoxy, butoxy), $C_1$-$C_2$-haloalkoxy (e.g. trifluoromethoxy), halogen (e.g. fluorine, chlorine, bromine, iodine), cyano or nitro, $R^4$ $C_1$-$C_6$alkyl ($C_1$-$C_4$-alkyl) (e.g. methyl, ethyl, n- or isopropyl, n-, iso-, sec- or tert-butyl, n-, iso-, sec-, tert- or neo-pentyl, hexyl) or aryl (e.g. phenyl), it being possible for the aromatic ring to be substituted by one or more, e.g. 1 to 5, in particular 1 to 3, of the following:

$C_1$-$C_4$-alkyl (e.g. methyl, ethyl, propyl, butyl), $C_1$-$C_2$-haloalkyl (e.g. trifluoromethyl, trichloromethyl), $C_1$-$C_4$-alkoxy (e.g. methoxy, ethoxy, propoxy, butoxy), $C_1$-$C_2$-haloalkoxy(e.g.difluoromethoxy,trifluoromethoxy),halogen (e.g. fluorine, chlorine, bromine, iodine),cyano or nitro, X CH or N.

The radical —C($R^4$)=N—O—$R^1$ on the phenyl can be in the 2 or, preferably, in the 3 or 4 position with respect to the —O—CH_2— radical.

Because of the C=C and C=N double bonds, preparation of the novel compounds of the general formula I may result in mixtures of E and Z isomers. These can be separated in a conventional manner, e.g. by crystallization or chromatography. The present invention relates both to the individual isomeric compounds and to mixtures thereof, and all of them can be used as fungicides. With regard to the —C(COOCH_3)=X—OCH_3 group, preferred compounds have the E configuration of the COOCH_3 and OCH_2 on the C=X double bond. With regard to the —C($R^4$)=N—O$R^1$ group, preferred compounds have the Z configuration of $R^4$ and O$R^1$ on the C=N double bond The novel compounds of the general formula I as claimed in claim 1 are prepared, for example, in such a way that a substituted oxime ether of the general formula II is reacted with a substituted benzyl compound of the general formula III where Y is a leaving group (e.g. chloride, bromide, p-toluenesulfonate, methanesulfonate, trifluoromethanesulfonate).

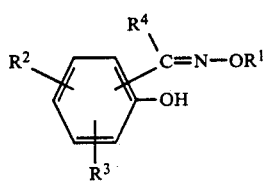

II

-continued

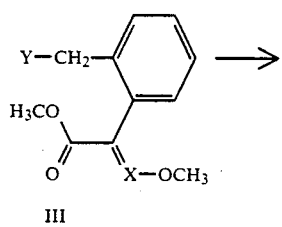

III

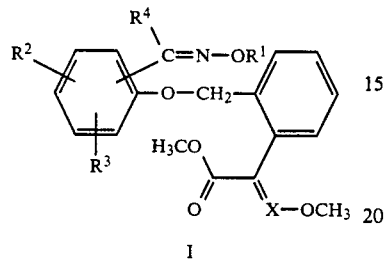

I $R^1$, $R^2$, $R^2$, $R^4$ and X have the abovementioned meanings.

These reactions can be carried out, for example, in an inert solvent or diluent (e.g. acetone, acetonitrile, dimethyl sulfoxide, dimethylformamide, N-methylpyrrolidone, N,N'-dimethylpropyleneurea or pyridine), using a base (e.g. sodium carbonate, potassium carbonate). It may also be advantageous to add a catalyst such as tris(3,6-dioxoheptyl)amine to the reaction mixture.

An alternative procedure is such that the compounds of the general formula II are initially converted with a base (e.g. sodium hydroxide, potassium hydroxide, sodium methanolate) into the corresponding sodium or potassium phenolates, and the latter are then reacted in an inert solvent or diluent (e.g. dimethylformamide) with the substituted benzyl compounds of the general formula III to give the compounds of the formula I according to the invention.

These reactions can also be carried out in a two-phase system (e.g. carbon tetrachloride/water). Examples of suitable phase-transfer catalysts are trioctylpropylammonium chloride or cetyltrimethylammonium chloride.

The substituted oxime ethers of the formula II required to prepare the novel compounds of the general formula I are either known or can be prepared by conventional processes.

Also required for the preparation of the compounds of the generally formula I according to the invention are the substituted benzyl compounds of the general formula III. Compounds of the general formula IIIa (X=N, Y=chloride, bromide) are obtained by halogenation of methyl 2-methylphenylglyoxylate O-methyloxime IV by literature methods. This is achieved, for example, with bromine or chlorine in an inert solvent (e.g. tetrachloromethane), with or without irradiation from a light source (e.g. Hg vapor lamp, 300W) or by reaction with N-chloro- or N-bromosuccinide (cf. Horner, Winkelmann, Angew. Chem. 71 (1959) 349).

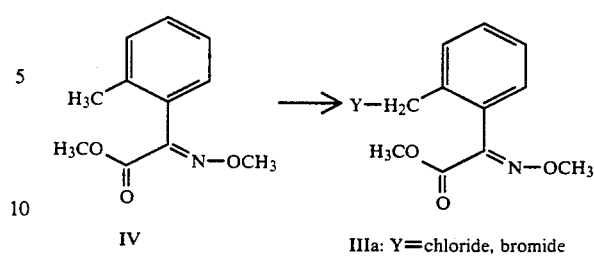

IIIa: Y=chloride, bromide

Methyl 2-methylphenylglyoxylate O-methyloxime IV can be prepared by reacting methyl 2-methylphenylglyoxylate V for example a) with O-methylhydroxylamine hydrochloride or b) with hydroxylamine hydrochloride to give the corresponding oxime and reacting the latter with a methylating agent of the formula $CH_3$-L where L is a leaving group (e.g. chloride, bromide, iodide, methylsulfate) (cf. DE 3,623,921).

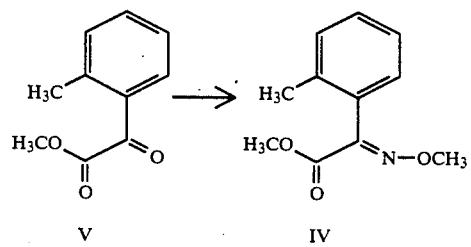

Benzyl halides of the generally formula IIIa (X=N, Y=chloride, bromide) are also obtained when methyl 2-halomethylphenylglyoxylates of the formula VI (Y=-chloride, bromide) are reacted a) with O-methylhydroxylamine hydrochloride or b) with hydroxylamine hydrochloride to give the corresponding oxime and reacting the latter with a methylating agent of the formula $CH_3$-L where L is a leaving group (e.g. chloride, bromide, iodide, methylsulfate) (cf. DE 3,623,921).

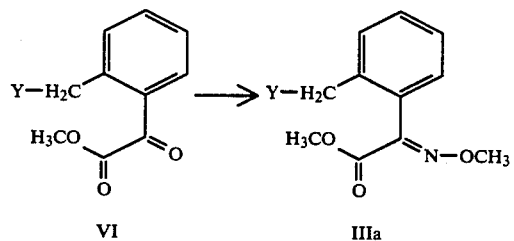

Y = chloride, bromide

Methyl 2-halomethylphenylglyoxylates of the formula VI (Y =chloride, bromide) can be prepared by halogenating methyl 2-methylphenylglyoxylate V by literature methods. The reaction is carried out, for example, with bromine or chlorine in an inert solvent (e.g. tetrachloromethane) with or without irradiation from a light source (e.g. Hg vapor lamp, 300 W) or with N-chloro- or N-bromosuccinimide (cf. Horner, Winkelmann, Angew. Chem. 71 (1959) 349).

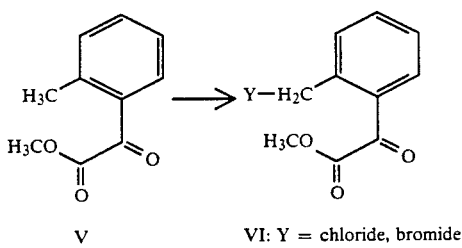

V    VI: Y = chloride, bromide

Substituted benzyl compounds of the general formula IIIb (X=CH, Y =chloride, bromide) are either known or can be prepared by conventional processes. Appropriate methods of preparation are described, for example, in DE 3,519,280, DE 3,545,318 and DE 3,545,319.

Substituted benzyl compounds of the general formula IIIc (X=CH or N, Y=p-toluenesulfonate, methanesulfonate, trifluoromethanesulfonate) can be prepared from the corresponding compounds of the general formula IIIa (X=N, Y=chloride, bromide) or IIIb (X=CH, Y=chloride, bromide) by reaction with p-toluenesulfonic acid (Y=p-toluenesulfonate), methanesulfonic acid (Y=methanesulfonate) or trifluoromethanesulfonic acid (Y=trifluoromethanesulfonate). The reactions can be carried out, for example, in an inert solvent or diluent (e.g. dimethylformamide) in the presence of a base (e.g. potassium carbonate). An alternative procedure is such that the appropriate sulfonic acid is initially converted into a sodium or potassium salt and the latter is then reacted in an inert solvent or diluent (e.g. dimethylformamide) with a compound of the general formula IIIa or IIIb to give the substituted benzyl compounds of the general formula IIIc.

The novel compounds of the general formula I can also be prepared by reacting the novel substituted carbonyl compounds of the general formula VII with a substituted hydroxylamine of the general formula VIII or with an acid addition salt (e.g. hydrochloride, hydrobromide) of VIII.

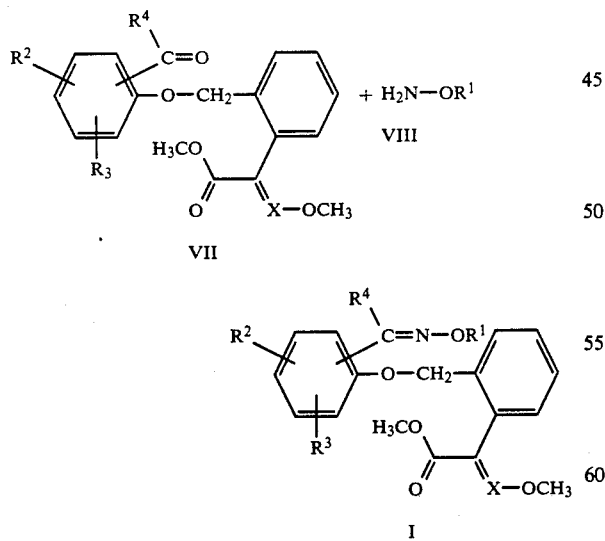

$R^1$, $R^2$, $R^3$, $R^4$ and X have the abovementioned meanings.

The reaction can be carried out in an inert solvent or diluent (e.g. methanol, ethanol, toluene) or in a two-phase system (e.g. toluene/water). It may also be advantageous to add a base (e.g. triethylamine, sodium carbonate, potassium carbonate, sodium bicarbonate, potassium bicarbonate, sodium hydroxide, potassium hydroxide) to the reaction mixture.

The novel carbonyl compounds of the general formula VII are required as starting compounds. These are obtained by reacting the substituted benzyl compounds of the general formula III where Y is a leaving group (e.g. chloride, bromide, p-toluenesulfonate, methanesulfonate, trifluoromethanesulfonate) with substituted carbonyl compounds of the general formula IX. The compounds of the general formula IX are known. They can be prepared by conventional processes.

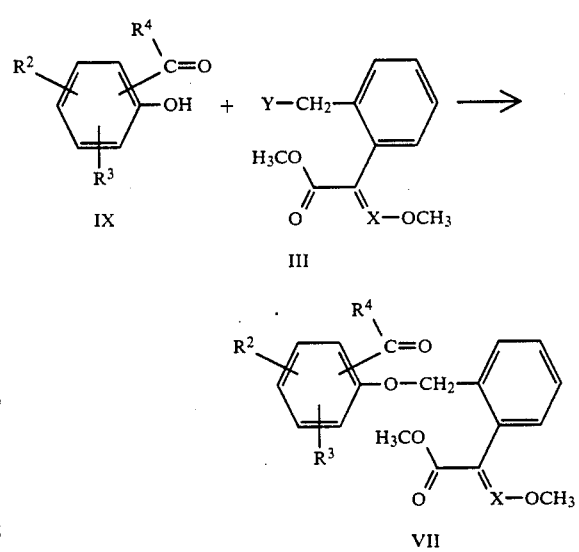

$R^1$, $R^2$, $R^3$, $R^4$ and X have the abovementioned meanings.

The examples and procedures which follow are intended to illustrate the preparation of the novel active ingredients and their precursors.

PROCEDURE 1

Methyl 2-bromomethylphenylglyoxylate O-methyloxime 21.4 g (0.133 mol) of bromine are added to a stirred solution of 27.5 g (0.133 mol) of methyl 2-methylphenylglyoxylate O-methyloxime in 400 ml of tetrachloromethane. The mixture is then refluxed while irradiating with a 300W Hg vapor lamp for four hours. It is then concentrated, the residue is taken up in ethyl acetate/water, and the organic phase is washed with $H_2O$, dried with sodium sulfate and evaporated. The crude product is purified by chromatography on silica gel with cyclohexane/ethyl acetate (9/1). 17.4 g (46%) of the abovementioned compound are obtained as an oil.

EXAMPLE 1

Methyl 2-(2-methoxyiminomethylphenoxymethyl)phenylglyoxylate O-methyloxime 3.0 g (20 mmol) of 2-hydroxybenzaldehyde O-methyloxime are dissolved in 20 ml of methanol, and 3.6 g (20 mmol) of sodium methanolate (30% strength in methanol) are added. The mixture is refluxed for four hours and then concentrated. The residue is taken up in 100 ml of dimethylformamide, and 6.5 g (23 mmol) of methyl 2-bromomethylphenylglyoxylate O-methyloxime in 50 ml of dimethylformamide are added. The mixture is stirred at 100° C. for 5 hours, the solvent is stripped off, and the residue is taken up in ethyl acetate. The organic phase is washed with water, dried and concentrated. The residue is triturated with pentane to induce crystallization. 4.8 g (67% of theory) of the title compound are obtained in the form of colorless crystals (melting point 73°–76° C., compound no. 2).

EXAMPLE 2

Methyl α-[2-(2-ethoxyiminomethylphenoxymethyl)phenyl]-β-methoxyacrylate 6.9 g (42 mmol) of 2-hydroxybenzaldehyde O-ethyloxime and 10.0 g (35 mmol) of methyl α-(2-bromometnylphenyl)-β-methoxyacrylate are dissolved in 100 ml of dimethylformamide, and 7.3 g (53 mmol) of potassium carbonate are added. The mixture is stirred at room temperature for 48 hours and then concentrated, and the residue is taken up in methylene chloride. The organic phase is washed with water, dried over MgSO4 and concentrated. The resulting oil is purified by chromatography on silica gel (cyclohexane/ethyl acetate). 8.4 g (65% of theory) of the title compound are obtained in the form of colorless crystals (melting point 86°–88° C., compound no. 23).

EXAMPLE 3

Methyl α-[2-(3-(1-ethoxyiminoethyl)phenoxymethyl)phenyl]-βmethoxycarylate 7.5 g (0.042 mol) of 3-(1-ethyoxyiminoethyl)phenol and 10.0 g (0.035 mol) methyl α-(2-bromomethyl-phenyl)-β-methoxyacrylate are dissolved in 100 ml of dimethylformamide, and 7.3, (0.053 mol) of potassium carbonate are added. The mixture is stirred at room temperature (20° C.) for 48 hours, hydrolyzed with water and extracted with diethyl ether. The organic phase is washed with water, dried over magnesium sulfate and concentrated. The resulting oil is purified by chromatography on alumina (cyclohexane). 7.3 g (54%) of the title compound are obtained as a colorless oil (compound no. 447).

EXAMPLE 4

Methyl 2-[3-(1-n-butoxyiminoethyl)phenoxymethyl]phenyl-glyoxylate O-methyloxime a) 3.0 g (0.022 mol) of 3-hydroxyacetophenone and 6.0 g (0.021 mol) of methyl 2-bromomethylphenyl-glyoxylate O-methyloxime are dissolved in 30 ml of dimethylformamide, and 5.5 g (0.040 yol) of potassium carbonate are added. The mixture is stirred at room temperature for 24 hours, hydrolyzed with water and extracted with methyl tert-butyl ether. The organic phase is washed with water, dried and concentrated. 5.8 g (85%) of methyl 2-(3-acetylphenoxymethyl)phenyl-glyoxylate O-methyloxime are obtained as a colorless oil.

5.8 g (0.017 mol) of methyl 2-(3-acetylphenoxymethyl)phenylglyoxylate O-methyloxime and 2.5 g (0.020 mol) of n-butoxyamine hydrochloride in 60 ml of methanol are stirred at room temperature for 24 hours. The mixture is then hydrolyzed with water and extracted with methyl tert-butyl ether. The organic phase is washed with water, dried and concentrated. 5.0 g (71%) of the title compound are obtained as a colorless oil (compound no. 470).

EXAMPLE 5

Methyl 2-[4-(1-benzyloxyiminoethyl)phenoxymethyl]phenyl-glyoxylate O-methyloxime a) 3.0 g (0.022 mol) of 4-hydroxyacetophenone and 6.0 g (0.021 mol) of methyl 2-bromomethylphenyl-glyoxylate O-methyloxime are dissolved in 30 ml of dimethylformamide, and 5.5 g (0.040 mol) of potassium carbonate are added. The mixture is stirred at room temperature for 24 hours, hydrolyzed with water and extracted with methyl tert-butyl ether. The organic phase is washed with water, dried and concentrated. 5.3 g (78%) of methyl 2-(4-acetylphenoxymethyl)phenyl-glyoxylate O-methyloxime are obtained as a colorless oil.

b) 5.3 g (0.016 mol) of methyl 2-(4-acetylphenoxymethyl)phenylglyoxylate O-methyloxime and 3.0 g (0.019 mol) of benzyloxyamine hydrochloride in 60 ml of methanol are stirred at room temperature for 24 hours. The mixture is then hydrolyzed with water and extracted with methyl tert-butyl ether. The organic phase is washed with water, dried and concentrated. 5.9 g (83%) of the title compound are obtained in the form of colorless crystals (melting point 104°–106° C., compound no. 590).

The compounds listed in Tables 1 to 3 can be prepared in a corresponding manner.

TABLE 1

Compounds of the general formula Ia (2-position of the oxime ether). The configuration statement (E) relates to the methyl β-methoxyacrylate group or the methyl glyoxylate O-methyloxime group.

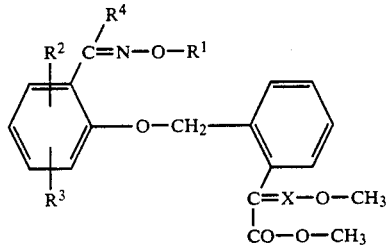

Ia

| Comp. no. | R¹ | R² | R³ | R⁴ | X | mp. (°C.) |
|---|---|---|---|---|---|---|
| 1 | CH₃— | H | H | H | CH | 82–84 (E) |
| 2 | CH₃— | H | H | H | N | 73–76 (E) |
| 3 | CH₃— | 4-Cl | H | H | CH | |
| 4 | CH₃— | 4-Cl | H | H | N | |
| 5 | CH₃— | 4-CH₃ | H | H | CH | |
| 6 | CH₃— | 4-CH₃ | H | H | N | |
| 7 | CH₃— | 4-OCH₃ | H | H | CH | |
| 8 | CH₃— | 4-OCH₃ | H | H | N | |
| 9 | CH₃— | 5-F | H | H | CH | |
| 10 | CH₃— | 5-F | H | H | N | |
| 11 | CH₃— | 5-Cl | H | H | CH | |
| 12 | CH₃— | 5-Cl | H | H | N | |
| 13 | CH₃— | 5-Br | H | H | CH | |
| 14 | CH₃— | 5-Br | H | H | N | |
| 15 | CH₃— | 5-CH₃ | H | H | CH | |
| 16 | CH₃— | 5-CH₃ | H | H | N | |
| 17 | CH₃— | 5-OCH₃ | H | H | CH | |
| 18 | CH₃— | 5-OCH₃ | H | H | N | |
| 19 | CH₃— | 6-OCH₃ | H | H | CH | |
| 20 | CH₃— | 6-OCH₃ | H | H | N | |
| 21 | CH₃— | 4-Cl | 6-Cl | H | CH | |
| 22 | CH₃— | 4-Cl | 6-Cl | H | N | |
| 23 | CH₃—CH₂— | H | H | H | CH | 86–88 (E) |
| 24 | CH₃—CH₂— | H | H | H | N | 89–90 (E) |
| 25 | CH₃—CH₂— | 4-Cl | H | H | CH | 95–97 (E) |
| 26 | CH₃—CH₂— | 4-Cl | H | H | N | |
| 27 | CH₃—CH₂— | 4-CH₃ | H | H | CH | |
| 28 | CH₃—CH₂— | 4-CH₃ | H | H | N | |
| 29 | CH₃—CH₂— | 4-OCH₃ | H | H | CH | |
| 30 | CH₃—CH₂— | 4-OCH₃ | H | H | N | |
| 31 | CH₃—CH₂— | 5-F | H | H | CH | |
| 32 | CH₃—CH₂— | 5-F | H | H | N | |
| 33 | CH₃—CH₂— | 5-Cl | H | H | CH | |
| 34 | CH₃—CH₂— | 5-Cl | H | H | N | |
| 35 | CH₃—CH₂— | 5-Br | H | H | CH | |
| 36 | CH₃—CH₂— | 5-Br | H | H | N | |
| 37 | CH₃—CH₂— | 5-CH₃ | H | H | CH | |
| 38 | CH₃—CH₂— | 5-CH₃ | H | H | N | |
| 39 | CH₃—CH₂— | 5-OCH₃ | H | H | CH | |
| 40 | CH₃—CH₂— | 5-OCH₃ | H | H | N | |
| 41 | CH₃—CH₂— | 6-OCH₃ | H | H | CH | |
| 42 | CH₃—CH₂— | 6-OCH₃ | H | H | N | |
| 43 | CH₃—CH₂— | 4-Cl | 6-Cl | H | CH | |
| 44 | CH₃—CH₂— | 4-Cl | 6-Cl | H | N | |
| 45 | CH₃—CH₂—CH₂— | H | H | H | CH | |
| 46 | CH₃—CH₂—CH₂— | H | H | H | N | |
| 47 | CH₂=CH—CH₂— | H | H | H | CH | |
| 48 | CH₂=CH—CH₂— | H | H | H | N | |
| 49 | CH₃—CH(CH₃)— | H | H | H | CH | |
| 50 | CH₃—CH(CH₃)— | H | H | H | N | |
| 51 | HC≡C—CH₂— | H | H | H | CH | |
| 52 | HC≡C—CH₂— | H | H | H | N | |
| 53 | cyclo-C₃H₅—CH₂— | H | H | H | CH | |
| 54 | cyclo-C₃H₅—CH₂— | H | H | H | N | |
| 55 | CH₃—CH₂—CH₂—CH₂— | H | H | H | CH | |
| 56 | CH₃—CH₂—CH₂—CH₂— | H | H | H | N | |
| 57 | CH₃—CH=CH—CH₂— | H | H | H | CH | |
| 58 | CH₃—CH=CH—CH₂— | H | H | H | N | |
| 59 | CH₃—(CH₂)₅— | H | H | H | CH | |
| 60 | CH₃—(CH₂)₅— | H | H | H | N | |
| 61 | cyclo-C₆H₁₁ | H | H | H | CH | |
| 62 | cyclo-C₆H₁₁— | H | H | H | N | |
| 63 | C₆H₅—CH₂— | H | H | H | CH | |
| 64 | C₆H₅—CH₂— | H | H | H | N | |
| 65 | 4-Cl—C₆H₄—CH₂— | H | H | H | CH | |
| 66 | 4-Cl—C₆H₄—CH₂— | H | H | H | N | |

TABLE 1-continued

Compounds of the general formula Ia (2-position of the oxime ether). The configuration statement (E) relates to the methyl β-methoxyacrylate group or the methyl glyoxylate O-methyloxime group.

Ia

| Comp. no. | R¹ | R² | R³ | R⁴ | X | mp. (°C.) |
|---|---|---|---|---|---|---|
| 67 | 3-CF₃—C₆H₄—CH₂— | H | H | H | CH | |
| 68 | 3-CF₃—C₆H₄—CH₂— | H | H | H | N | |
| 69 | 4-Cl—C₆H₄—CH₂—CH₂— | H | H | H | CH | |
| 70 | 4-Cl—C₆H₄—CH₂—CH₂— | H | H | H | N | |
| 71 | C₆H₅—CH₂—CH₂—CH₂— | H | H | H | CH | |
| 72 | C₆H₅—CH₂—CH₂—CH₂— | H | H | H | N | |
| 73 | C₆H₅—(CH₂)₄— | H | H | H | CH | |
| 74 | C₆H₅—(CH₂)₄— | H | H | H | N | |
| 75 | C₆H₅—CH₂—CH=CH—CH₂— | H | H | H | CH | |
| 76 | C₆H₅—CH₂—CH=CH—CH₂— | H | H | H | N | |
| 77 | 4-F—C₆H₄—CH=CH—CH₂—CH₂— | H | H | H | CH | |
| 78 | 4-F—C₆H₄—CH=CH—CH₂—CH₂— | H | H | H | N | |
| 79 | t-C₄H₉O—CO—CH₂— | H | H | H | CH | |
| 80 | t-C₄H₉O—CO—CH₂— | H | H | H | N | |
| 81 | t-C₄H₉O—CO—(CH₂)₃— | H | H | H | CH | |
| 82 | t-C₄H₉O—CO—(CH₂)₃— | H | H | H | N | |
| 83 | Cl—CH=CH—CH₂— | H | H | H | CH | |
| 84 | Cl—CH=CH—CH₂— | H | H | H | N | |
| 221 | C₂H₅ | 6-OC₂H₅ | H | H | CH | |
| 222 | C₂H₅ | 6-OC₂H₅ | H | H | N | |
| 223 | CH₃—C(CH₃)₂— | H | H | H | CH | |
| 224 | CH₃—C(CH₃)₂— | H | H | H | N | |
| 225 | CH₃—CH(CH₃)—CH₂— | H | H | H | CH | |
| 226 | CH₃—CH(CH₃)—CH₂— | H | H | H | N | |
| 227 | CH₂=C(CH₃)—CH₂— | H | H | H | CH | |
| 228 | CH₂=C(CH₃)—CH₂— | H | H | H | N | |
| 229 | CH₃—CH(CH₃)—CH₂—CH₂— | H | H | H | CH | |
| 230 | CH₃—CH(CH₃)—CH₂—CH₂— | H | H | H | N | |
| 231 | CH₃—(CH₂)₄— | H | H | H | CH | |
| 232 | CH₃—(CH₂)₄— | H | H | H | N | |
| 233 | 2-F—C₆H₄—CH₂— | H | H | H | CH | |
| 234 | 2-F—C₆H₄—CH₂— | H | H | H | N | |
| 235 | 3-F—C₆H₄—CH₂— | H | H | H | CH | |
| 236 | 3-F—C₆H₄—CH₂— | H | H | H | N | |
| 237 | 2-Cl—C₆H₄—CH₂— | H | H | H | CH | |
| 238 | 2-Cl—C₆H₄—CH₂— | H | H | H | N | |
| 239 | 3,4-Cl₂—C₆H₃—CH₂— | H | H | H | CH | |
| 240 | 3,4-Cl₂—C₆H₃—CH₂— | H | H | H | N | |
| 241 | 2,6-Cl₂—C₆H₃—CH₂— | H | H | H | CH | |
| 242 | 2,6-Cl₂—C₆H₃—CH₂— | H | H | H | N | |
| 243 | C₆H₅—CH₂—CH₂— | H | H | H | CH | |
| 244 | C₆H₅—CH₂—CH₂— | H | H | H | N | |
| 245 | C₆H₅—CH=CH—CH₂—CH₂— | H | H | H | CH | |
| 246 | C₆H₅—CH=CH—CH₂—CH₂— | H | H | H | N | |
| 247 | 4-Cl—C₆H₄—CH₂—CH=CH—CH₂— | H | H | H | CH | |
| 248 | 4-Cl—C₆H₄—CH₂—CH=CH—CH₂— | H | H | H | N | |
| 249 | 4-CF₃—C₆H₄—CH₂—CH=CH—CH₂— | H | H | H | CH | |
| 250 | 4-CF₃—C₆H₄—CH₂—CH=CH—CH₂— | H | H | H | N | |
| 311 | CH₃ | H | H | CH₃ | CH | |
| 312 | CH₃ | H | H | CH₃ | N | |
| 313 | CH₃ | 4-Cl | H | CH₃ | CH | |
| 314 | CH₃ | 4-Cl | H | CH₃ | N | |
| 315 | CH₃ | 4-CH₃ | H | CH₃ | CH | |
| 316 | CH₃ | 4-CH₃ | H | CH₃ | N | |
| 317 | CH₃ | 4-OCH₃ | H | CH₃ | CH | |
| 318 | CH₃ | 4-OCH₃ | H | CH₃ | N | |
| 319 | CH₃ | 5-F | H | CH₃ | CH | |
| 320 | CH₃ | 5-F | H | CH₃ | N | |
| 321 | CH₃ | 5-Cl | H | CH₃ | CH | |
| 322 | CH₃ | 5-Cl | H | CH₃ | N | |
| 323 | CH₃ | 5-Br | H | CH₃ | CH | |
| 324 | CH₃ | 5-Br | H | CH₃ | N | |
| 325 | CH₃ | 5-CH₃ | H | CH₃ | CH | |
| 326 | CH₃ | 5-CH₃ | H | CH₃ | N | |
| 327 | CH₃ | 5-OCH₃ | H | CH₃ | CH | |
| 328 | CH₃ | 5-OCH₃ | H | CH₃ | N | |

TABLE 1-continued

Compounds of the general formula Ia (2-position of the oxime ether). The configuration statement (E) relates to the methyl β-methoxyacrylate group or the methyl glyoxylate O-methyloxime group.

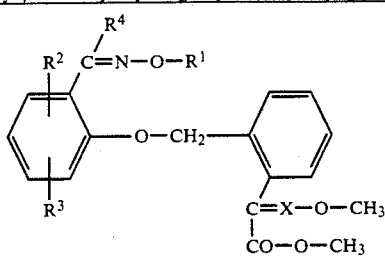

Ia

| Comp. no. | R¹ | R² | R³ | R⁴ | X | mp. (°C.) |
|---|---|---|---|---|---|---|
| 329 | CH₃ | 6-OCH₃ | H | CH₃ | CH | |
| 330 | CH₃ | 6-OCH₃ | H | CH₃ | N | |
| 331 | CH₃ | 4-Cl | 6-Cl | CH₃ | CH | |
| 332 | CH₃ | 4-Cl | 6-Cl | CH₃ | N | |
| 333 | CH₃—CH₂ | H | H | CH₃ | CH | |
| 334 | CH₃—CH₂ | H | H | CH₃ | N | |
| 335 | CH₃—CH₂ | 4-Cl | H | CH₃ | CH | |
| 336 | CH₃—CH₂ | 4-Cl | H | CH₃ | N | |
| 337 | CH₃—CH₂ | 4-CH₃ | H | CH₃ | CH | |
| 338 | CH₃—CH₂ | 4-CH₃ | H | CH₃ | N | |
| 339 | CH₃—CH₂ | 4-OCH₃ | H | CH₃ | CH | |
| 340 | CH₃—CH₂ | 4-OCH₃ | H | CH₃ | N | |
| 341 | CH₃—CH₂ | 5-F | H | CH₃ | CH | |
| 342 | CH₃—CH₂ | 5-F | H | CH₃ | N | |
| 343 | CH₃—CH₂ | 5-Cl | H | CH₃ | CH | |
| 344 | CH₃—CH₂ | 5-Cl | H | CH₃ | N | |
| 345 | CH₃—CH₂ | 5-Br | H | CH₃ | CH | |
| 346 | CH₃—CH₂ | 5-Br | H | CH₃ | N | |
| 347 | CH₃—CH₂ | 5-CH₃ | H | CH₃ | CH | |
| 348 | CH₃—CH₂ | 5-CH₃ | H | CH₃ | N | |
| 349 | CH₃—CH₂ | 5-OCH₃ | H | CH₃ | CH | |
| 350 | CH₃—CH₂ | 5-OCH₃ | H | CH₃ | N | |
| 351 | CH₃—CH₂ | 6-OCH₃ | H | CH₃ | CH | |
| 352 | CH₃—CH₂ | 6-OCH₃ | H | CH₃ | N | |
| 353 | CH₃—CH₂ | 4-Cl | 6-Cl | CH₃ | CH | |
| 354 | CH₃—CH₂ | 4-Cl | 6-Cl | CH₃ | N | |
| 355 | CH₃—CH₂—CH₂ | H | H | CH₃ | CH | |
| 356 | CH₃—CH₂—CH₂ | H | H | CH₃ | N | |
| 357 | CH₂=CH—CH₂ | H | H | CH₃ | CH | |
| 358 | CH₂=CH—CH₂ | H | H | CH₃ | N | |
| 359 | CH₃—CH(CH₃) | H | H | CH₃ | CH | |
| 360 | CH₃—CH(CH₃) | H | H | CH₃ | N | |
| 361 | HC≡C—CH₂ | H | H | CH₃ | CH | |
| 362 | HC≡C—CH₂ | H | H | CH₃ | N | |
| 363 | cyclo-C₃H₅—CH₂ | H | H | CH₃ | CH | |
| 364 | cyclo-C₃H₅—CH₂ | H | H | CH₃ | N | |
| 365 | CH₃—CH₂—CH₂—CH₂ | H | H | CH₃ | CH | |
| 366 | CH₃—CH₂—CH₂—CH₂ | H | H | CH₃ | N | |
| 367 | CH₃—CH=CH—CH₂ | H | H | CH₃ | CH | |
| 368 | CH₃—CH=CH—CH₂ | H | H | CH₃ | N | |
| 369 | CH₃—(CH₂)₅ | H | H | CH₃ | CH | |
| 370 | CH₃—(CH₂)₅ | H | H | CH₃ | N | |
| 371 | cyclo-C₆H₁₁ | H | H | CH₃ | CH | |
| 372 | cyclo-C₆H₁₁ | H | H | CH₃ | N | |
| 373 | C₆H₅—CH₂ | H | H | CH₃ | CH | |
| 374 | C₆H₅—CH₂ | H | H | CH₃ | N | |
| 375 | 4-Cl—C₆H₄—CH₂ | H | H | CH₃ | CH | |
| 376 | 4-Cl—C₆H₄—CH₂ | H | H | CH₃ | N | |
| 377 | 3-CF₃—C₆H₄—CH₂ | H | H | CH₃ | CH | |
| 378 | 3-CF₃—C₆H₄—CH₂ | H | H | CH₃ | N | |
| 379 | 4-Cl—C₆H₄—CH₂—CH₂ | H | H | CH₃ | CH | |
| 380 | 4-Cl—C₆H₄—CH₂—CH₂ | H | H | CH₃ | N | |
| 381 | C₆H₅—CH₂—CH₂—CH₂ | H | H | CH₃ | CH | |
| 382 | C₆H₅—CH₂—CH₂—CH₂ | H | H | CH₃ | N | |
| 383 | C₆H₅—(CH₂)₄ | H | H | CH₃ | CH | |
| 384 | C₆H₅—(CH₂)₄ | H | H | CH₃ | N | |
| 385 | C₆H₅—CH₂—CH=CH—CH₂ | H | H | CH₃ | CH | |
| 386 | C₆H₅—CH₂—CH=CH—CH₂ | H | H | CH₃ | N | |
| 387 | 4-F—C₆H₄—CH=CH—CH₂—CH₂ | H | H | CH₃ | CH | |
| 388 | 4-F—C₆H₄—CH=CH—CH₂—CH₂ | H | H | CH₃ | N | |
| 389 | t-C₄H₉O—CO—CH₂ | H | H | CH₃ | CH | |
| 390 | t-C₄H₉O—CO—CH₂ | H | H | CH₃ | N | |
| 391 | t-C₄H₉O—CO—(CH₂)₃ | H | H | CH₃ | CH | |
| 392 | t-C₄H₉O—CO—(CH₂)₃ | H | H | CH₃ | N | |
| 393 | Cl—CH=CH—CH₂ | H | H | CH₃ | CH | |
| 394 | Cl—CH=CH—CH₂ | H | H | CH₃ | N | |

TABLE 1-continued

Compounds of the general formula Ia (2-position of the oxime ether). The configuration statement (E) relates to the methyl β-methoxyacrylate group or the methyl glyoxylate O-methyloxime group.

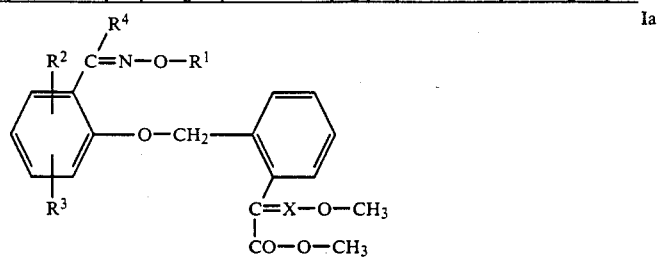

Ia

| Comp. no. | R¹ | R² | R³ | R⁴ | X | mp. (°C.) |
|---|---|---|---|---|---|---|
| 395 | $C_2H_5$ | 6-$OC_2H_5$ | H | $CH_3$ | CH | |
| 396 | $C_2H_5$ | 6-$OC_2H_5$ | H | $CH_3$ | N | |
| 397 | $CH_3-C(CH_3)_2$ | H | H | $CH_3$ | CH | |
| 398 | $CH_3-C(CH_3)_2$ | H | H | $CH_3$ | N | |
| 399 | $CH_3-CH(CH_3)-CH_2$ | H | H | $CH_3$ | CH | |
| 400 | $CH_3-CH(CH_3)-CH_2$ | H | H | $CH_3$ | N | |
| 401 | $CH_2=C(CH_3)-CH_2$ | H | H | $CH_3$ | CH | |
| 402 | $CH_2=C(CH_3)-CH_2$ | H | H | $CH_3$ | N | |
| 403 | $CH_3-CH(CH_3)-CH_2-CH_2$ | H | H | $CH_3$ | CH | |
| 404 | $CH_3-CH(CH_3)-CH_2-CH_2$ | H | H | $CH_3$ | N | |
| 405 | $CH_3-(CH_2)_4$ | H | H | $CH_3$ | CH | |
| 406 | $CH_3-(CH_2)_4$ | H | H | $CH_3$ | N | |
| 407 | 2-F-$C_6H_4$-$CH_2$ | H | H | $CH_3$ | CH | |
| 408 | 2-F-$C_6H_4$-$CH_2$ | H | H | $CH_3$ | N | |
| 409 | 3-F-$C_6H_4$-$CH_2$ | H | H | $CH_3$ | CH | |
| 410 | 3-F-$C_6H_4$-$CH_2$ | H | H | $CH_3$ | N | |
| 411 | 2-Cl-$C_6H_4$-$CH_2$ | H | H | $CH_3$ | CH | |
| 412 | 2-Cl-$C_6H_4$-$CH_2$ | H | H | $CH_3$ | N | |
| 413 | 3,4-$Cl_2$-$C_6H_3$-$CH_2$ | H | H | $CH_3$ | CH | |
| 414 | 3,4-$Cl_2$-$C_6H_3$-$CH_2$ | H | H | $CH_3$ | N | |
| 415 | 2,6-$Cl_2$-$C_6H_3$-$CH_2$ | H | H | $CH_3$ | CH | |
| 416 | 2,6-$Cl_2$-$C_6H_3$-$CH_2$ | H | H | $CH_3$ | N | |
| 417 | $C_6H_5$-$CH_2$-$CH_2$ | H | H | $CH_3$ | CH | |
| 418 | $C_6H_5$-$CH_2$-$CH_2$ | H | H | $CH_3$ | N | |
| 419 | $C_6H_5$-CH=CH-$CH_2$-$CH_2$ | H | H | $CH_3$ | CH | |
| 420 | $C_6H_5$-CH=CH-$CH_2$-$CH_2$ | H | H | $CH_3$ | N | |
| 421 | 4-Cl-$C_6H_4$-$CH_2$-CH=CH-$CH_2$ | H | H | $CH_3$ | CH | |
| 422 | 4-Cl-$C_6H_4$-$CH_2$-CH=CH-$CH_2$ | H | H | $CH_3$ | N | |
| 423 | 4-$CF_3$-$C_6H_4$-$CH_2$-CH=CH-$CH_2$ | H | H | $CH_3$ | CH | |
| 424 | 4-$CF_3$-$C_6H_4$-$CH_2$-CH=CH-$CH_2$ | H | H | $CH_3$ | N | |
| 425 | $CH_3$ | H | H | $C_6H_5$ | CH | |
| 426 | $CH_3$ | H | H | $C_6H_5$ | N | |
| 427 | $C_2H_5$ | H | H | $C_6H_5$ | CH | |
| 428 | $C_2H_5$ | H | H | $C_6H_5$ | N | |
| 429 | $CH_3$-$CH_2$-$CH_2$ | H | H | | CH | |
| 430 | $CH_3$-$CH_2$-$CH_2$ | H | H | $C_6H_5$ | N | |
| 431 | $CH_3$-$(CH_2)_5$ | H | H | $C_6H_5$ | CH | |
| 432 | $CH_3$-$(CH_2)_5$ | H | H | $C_6H_5$ | N | |
| 433 | $C_6H_5$-$CH_2$ | H | H | $C_6H_5$ | CH | |
| 434 | $C_6H_5$-$CH_2$ | H | H | $C_6H_5$ | N | |

TABLE 2

Compounds of the general formula Ib (3-position of the oxime ether). The configuration statement relates to the methyl β-methoxyacrylate group or the methyl glyoxylate O-methyloxime group.

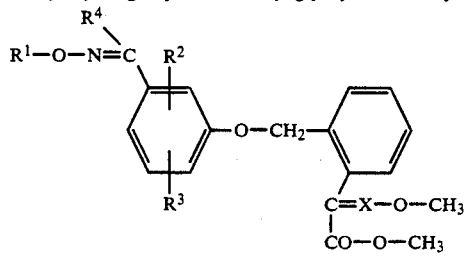

Ib

| Comp. no. | R¹ | R² | R³ | R⁴ | X | mp. (°C.) |
|---|---|---|---|---|---|---|
| 85 | $CH_3-$ | H | H | H | CH | 75-77 (E) |
| 86 | $CH_3-$ | H | H | H | N | oil (E) |
| 87 | $CH_3-$ | 2-Cl | 5-Cl | H | CH | |
| 88 | $CH_3-$ | 2-Cl | 5-Cl | H | N | |

TABLE 2-continued

Compounds of the general formula Ib (3-position of the oxime ether).
The configuration statement relates to the
methyl β-methoxyacrylate group or the methyl glyoxylate O-methyloxime group.

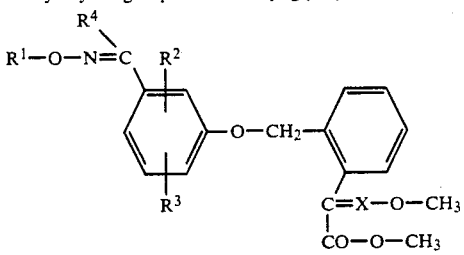

| Comp. no. | R¹ | R² | R³ | R⁴ | X | mp. (°C.) |
|---|---|---|---|---|---|---|
| 89 | CH₃— | 4-Cl | H | H | CH | |
| 90 | CH₃— | 4-Cl | H | H | N | |
| 91 | CH₃— | 4-CH₃ | H | H | CH | |
| 92 | CH₃— | 4-CH₃ | H | H | N | |
| 93 | CH₃— | 5-OCH₃ | H | H | CH | |
| 94 | CH₃— | 5-OCH₃ | H | H | N | |
| 95 | CH₃— | 6-OCH₃ | H | H | CH | |
| 96 | CH₃— | 6-OCH₃ | H | H | N | |
| 97 | CH₃—CH₂— | H | H | H | CH | oil (E) |
| 98 | CH₃—CH₂— | H | H | H | N | oil (E) |
| 99 | CH₃—CH₂— | 2-Cl | 5-Cl | H | CH | |
| 100 | CH₃—CH₂— | 2-Cl | 5-Cl | H | N | |
| 101 | CH₃—CH₂— | 4-Cl | H | H | CH | |
| 102 | CH₃—CH₂— | 4-Cl | H | H | N | |
| 103 | CH₃—CH₂— | 4-CH₃ | H | H | CH | |
| 104 | CH₃—CH₂— | 4-CH₃ | H | H | N | |
| 105 | CH₃—CH₂— | 5-OCH₃ | H | H | CH | |
| 106 | CH₃—CH₂— | 5-OCH₃ | H | H | N | |
| 107 | CH₃—CH₂— | 6-OCH₃ | H | H | CH | 96-98 (E) |
| 108 | CH₃—CH₂— | 6-OCH₃ | H | H | N | 124-126 (E) |
| 109 | CH₃—CH₂—CH₂— | H | H | H | CH | |
| 110 | CH₃—CH₂—CH₂— | H | H | H | N | |
| 111 | CH₂=CH—CH₂— | H | H | H | CH | oil (E) |
| 112 | CH₂=CH—CH₂— | H | H | H | N | oil (E) |
| 113 | CH₃—CH(CH₃)— | H | H | H | CH | oil (E) |
| 114 | CH₃—CH(CH₃)— | H | H | H | N | oil (E) |
| 115 | HC≡C—CH₂— | H | H | H | CH | |
| 116 | HC≡C—CH₂— | H | H | H | N | |
| 117 | cyclo-C₃H₅—CH₂— | H | H | H | CH | |
| 118 | cyclo-C₃H₅—CH₂— | H | H | H | N | |
| 119 | CH₃—CH₂—CH₂—CH₂— | H | H | H | CH | oil (E) |
| 120 | CH₃—CH₂—CH₂—CH₂— | H | H | H | N | oil (E) |
| 121 | CH₃—CH=CH—CH₂— | H | H | H | CH | |
| 122 | CH₃—CH=CH—CH₂— | H | H | H | N | |
| 123 | CH₃—(CH₂)₅— | H | H | H | CH | oil (E) |
| 124 | CH₃—(CH₂)₅— | H | H | H | N | oil (E) |
| 125 | cyclo-C₆H₁₁— | H | H | H | CH | |
| 126 | cyclo-C₆H₁₁— | H | H | H | N | |
| 127 | C₆H₅—CH₂— | H | H | H | CH | oil (E) |
| 128 | C₆H₅—CH₂— | H | H | H | N | oil (E) |
| 129 | 4-Cl—C₆H₄—CH₂— | H | H | H | CH | |
| 130 | 4-Cl—C₆H₄—CH₂— | H | H | H | N | |
| 131 | 3-CF₃—C₆H₄—CH₂— | H | H | H | CH | |
| 132 | 3-CF₃—C₆H₄—CH₂— | H | H | H | N | |
| 133 | 4-Cl—C₆H₄—CH₂—CH₂— | H | H | H | CH | |
| 134 | 4-Cl—C₆H₄—CH₂—CH₂— | H | H | H | N | |
| 135 | C₆H₅—CH₂—CH₂—CH₂— | H | H | H | CH | |
| 136 | C₆H₅—CH₂—CH₂—CH₂— | H | H | H | N | |
| 137 | C₆H₅—(CH₂)₄— | H | H | H | CH | |
| 138 | C₆H₅—(CH₂)₄— | H | H | H | N | |
| 139 | C₆H₅—CH₂—CH=CH—CH₂— | H | H | H | CH | |
| 140 | C₆H₅—CH₂—CH=CH—CH₂— | H | H | H | N | |
| 141 | 4-F—C₆H₄—CH=CH—CH₂—CH₂— | H | H | H | CH | |
| 142 | 4-F—C₆H₄—CH=CH—CH₂—CH₂— | H | H | H | N | |
| 143 | t-C₄H₉O—CO—CH₂— | H | H | H | CH | |
| 144 | t-C₄H₉O—CO—CH₂— | H | H | H | N | |
| 145 | t-C₄H₉O—CO—(CH₂)₃— | H | H | H | CH | |
| 146 | t-C₄H₉O—CO—(CH₂)₃— | H | H | H | N | |
| 147 | Cl—CH=CH—CH₂— | H | H | H | CH | |
| 148 | Cl—CH=CH—CH₂— | H | H | H | N | |
| 251 | C₂H₅ | 6-OC₂H₅ | H | H | CH | 83-85 (E) |
| 252 | C₂H₅ | 6-OC₂H₅ | H | H | N | 104-106 (E) |
| 253 | CH₃—C(CH₃)₂— | H | H | H | CH | |
| 254 | CH₃—C(CH₃)₂— | H | H | H | N | |
| 255 | CH₃—CH(CH₃)—CH₂— | H | H | H | CH | |

TABLE 2-continued

Compounds of the general formula Ib (3-position of the oxime ether).
The configuration statement relates to the
methyl β-methoxyacrylate group or the methyl glyoxylate O-methyloxime group.

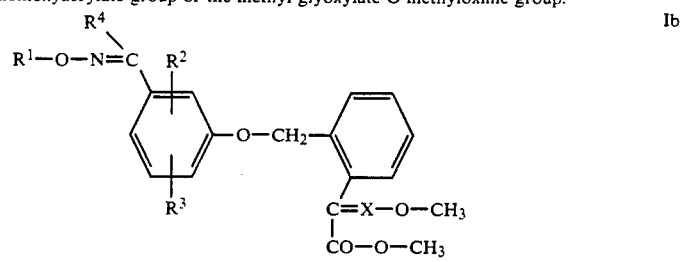

Ib

| Comp. no. | $R^1$ | $R^2$ | $R^3$ | $R^4$ | X | mp. (°C.) |
|---|---|---|---|---|---|---|
| 256 | $CH_3-CH(CH_3)-CH_2-$ | H | H | H | N | |
| 257 | $CH_2=C(CH_3)-CH_2$ | H | H | H | CH | |
| 258 | $CH_2=C(CH_3)-CH_2$ | H | H | H | N | |
| 259 | $CH_3-CH(CH_3)-CH_2-CH_2-$ | H | H | H | CH | |
| 260 | $CH_3-CH(CH_3)-CH_2-CH_2-$ | H | H | H | N | |
| 261 | $CH_3-(CH_2)_4-$ | H | H | H | CH | |
| 262 | $CH_3-(CH_2)_4-$ | H | H | H | N | oil (E) |
| 263 | $2-F-C_6H_4-CH_2-$ | H | H | H | CH | oil (E) |
| 264 | $2-F-C_6H_4-CH_2-$ | H | H | H | N | oil (E) |
| 265 | $3-F-C_6H_4-CH_2-$ | H | H | H | CH | oil (E) |
| 266 | $3-F-C_6H_4-CH_2-$ | H | H | H | N | oil (E) |
| 267 | $2-Cl-C_6H_4-CH_2-$ | H | H | H | CH | oil (E) |
| 268 | $2-Cl-C_6H_4-CH_2-$ | H | H | H | N | |
| 269 | $3,4-Cl_2-C_6H_3-CH_2-$ | H | H | H | CH | oil (E) |
| 270 | $3,4-Cl_2-C_6H_3-CH_2-$ | H | H | H | N | oil (E) |
| 271 | $2,6-Cl_2-C_6H_3-CH_2-$ | H | H | H | CH | oil (E) |
| 272 | $2,6-Cl_2-C_6H_3-CH_2-$ | H | H | H | N | oil (E) |
| 273 | $C_6H_5-CH_2-CH_2-$ | H | H | H | CH | oil (E) |
| 274 | $C_6H_5-CH_2-CH_2-$ | H | H | H | N | oil (E) |
| 275 | $C_6H_5-CH=CH-CH_2-CH_2-$ | H | H | H | CH | oil (E) |
| 276 | $C_6H_5-CH=CH-CH_2-CH_2-$ | H | H | H | N | oil (E) |
| 277 | $4-Cl-C_6H_4-CH_2-CH=CH-CH_2-$ | H | H | H | CH | oil (E) |
| 278 | $4-Cl-C_6H_4-CH_2-CH=CH-CH_2-$ | H | H | H | N | oil (E) |
| 279 | $4-CF_3-C_6H_4-CH_2-CH=CH-CH_2-$ | H | H | H | CH | oil (E) |
| 280 | $4-CF_3-C_6H_4-CH_2-CH=CH-CH_2-$ | H | H | H | N | oil (E) |
| 435 | $CH_3$ | H | H | $CH_3$ | CH | oil (E) |
| 436 | $CH_3$ | H | H | $CH_3$ | N | oil (E) |
| 437 | $CH_3$ | 2-Cl | 5-Cl | $CH_3$ | CH | |
| 438 | $CH_3$ | 2-Cl | 5-Cl | $CH_3$ | N | |
| 439 | $CH_3$ | 4-Cl | H | $CH_3$ | CH | |
| 440 | $CH_3$ | 4-Cl | H | $CH_3$ | N | |
| 441 | $CH_3$ | $4-CH_3$ | H | $CH_3$ | CH | |
| 442 | $CH_3$ | $4-CH_3$ | H | $CH_3$ | N | |
| 443 | $CH_3$ | $5-OCH_3$ | H | $CH_3$ | CH | |
| 444 | $CH_3$ | $5-OCH_3$ | H | $CH_3$ | N | |
| 445 | $CH_3$ | $6-OCH_3$ | H | $CH_3$ | CH | |
| 446 | $CH_3$ | $6-OCH_3$ | H | $CH_3$ | N | |
| 447 | $CH_3-CH_2$ | H | H | $CH_3$ | CH | oil (E) |
| 448 | $CH_3-CH_2$ | H | H | $CH_3$ | N | oil (E) |
| 449 | $CH_3-CH_2$ | 2-Cl | 5-Cl | $CH_3$ | CH | |
| 450 | $CH_3-CH_2$ | 2-Cl | 5-Cl | $CH_3$ | N | |
| 451 | $CH_3-CH_2$ | 4-Cl | H | $CH_3$ | CH | |
| 452 | $CH_3-CH_2$ | 4-Cl | H | $CH_3$ | N | |
| 453 | $CH_3-CH_2$ | $4-CH_3$ | H | $CH_3$ | CH | |
| 454 | $CH_3-CH_2$ | $4-CH_3$ | H | $CH_3$ | N | |
| 455 | $CH_3-CH_2$ | $5-OCH_3$ | H | $CH_3$ | CH | |
| 456 | $CH_3-CH_2$ | $5-OCH_3$ | H | $CH_3$ | N | |
| 457 | $CH_3-CH_2$ | $6-OCH_3$ | H | $CH_3$ | CH | |
| 458 | $CH_3-CH_2$ | $6-OCH_3$ | H | $CH_3$ | N | |
| 459 | $CH_3-CH_2-CH_2$ | H | H | $CH_3$ | CH | oil (E) |
| 460 | $CH_3-CH_2-CH_2$ | H | H | $CH_3$ | N | 73-74 (E) |
| 461 | $CH_2=CH-CH_2$ | H | H | $CH_3$ | CH | oil (E) |
| 462 | $CH_2=CH-CH_2$ | H | H | $CH_3$ | N | 51-53 (E) |
| 463 | $CH_3-CH(CH_3)$ | H | H | $CH_3$ | CH | oil (E) |
| 464 | $CH_3-CH(CH_3)$ | H | H | $CH_3$ | N | 58-60 (E) |
| 465 | $HC\equiv C-CH_2$ | H | H | $CH_3$ | CH | |
| 466 | $HC\equiv C-CH_2$ | H | H | $CH_3$ | N | |
| 467 | cyclo-$C_3H_5-CH_2$ | H | H | $CH_3$ | CH | |
| 468 | cyclo-$C_3H_5-CH_2$ | H | H | $CH_3$ | N | |
| 469 | $CH_3-CH_2-CH_2-CH_2$ | H | H | $CH_3$ | CH | oil (E) |
| 470 | $CH_3-CH_2-CH_2-CH_2$ | H | H | $CH_3$ | N | oil (E) |
| 471 | $CH_3-CH=CH-CH_2$ | H | H | $CH_3$ | CH | oil (E) |
| 472 | $CH_3-CH=CH-CH_2$ | H | H | $CH_3$ | N | 76-78 (E) |
| 473 | $CH_3-(CH_2)_5$ | H | H | $CH_3$ | CH | oil (E) |
| 474 | $CH_3-(CH_2)_5$ | H | H | $CH_3$ | N | oil (E) |

TABLE 2-continued

Compounds of the general formula Ib (3-position of the oxime ether).
The configuration statement relates to the
methyl β-methoxyacrylate group or the methyl glyoxylate O-methyloxime group.

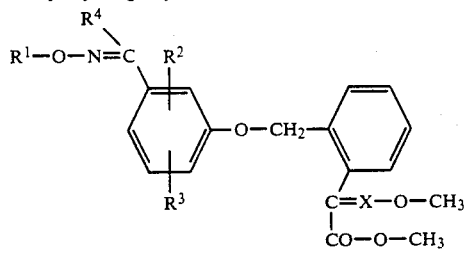

| Comp. no. | R¹ | R² | R³ | R⁴ | X | mp. (°C.) |
|---|---|---|---|---|---|---|
| 475 | cyclo-C₆H₁₁ | H | H | CH₃ | CH | |
| 476 | cyclo-C₆H₁₁ | H | H | CH₃ | N | |
| 477 | C₆H₅—CH₂ | H | H | CH₃ | CH | |
| 478 | C₆H₅—CH₂ | H | H | CH₃ | N | oil (E) |
| 479 | 4-Cl—C₆H₄—CH₂ | H | H | CH₃ | CH | |
| 480 | 4-Cl—C₆H₄—CH₂ | H | H | CH₃ | N | |
| 481 | 3-CF₃—C₆H₄—CH₂ | H | H | CH₃ | CH | |
| 482 | 3-CF₃—C₆H₄—CH₂ | H | H | CH₃ | N | |
| 483 | 4-Cl—C₆H₄—CH₂—CH₂ | H | H | CH₃ | CH | |
| 484 | 4-Cl—C₆H₄—CH₂—CH₂ | H | H | CH₃ | N | |
| 485 | C₆H₅—CH₂—CH₂—CH₂ | H | H | CH₃ | CH | |
| 486 | C₆H₅—CH₂—CH₂—CH₂ | H | H | CH₃ | N | |
| 487 | C₆H₅—(CH₂)₄ | H | H | CH₃ | CH | |
| 488 | C₆H₅—(CH₂)₄ | H | H | CH₃ | N | |
| 489 | C₆H₅—CH₂—CH=CH—CH₂ | H | H | CH₃ | CH | |
| 490 | C₆H₅—CH₂—CH=CH—CH₂ | H | H | CH₃ | N | |
| 491 | 4-F—C₆H₄—CH=CH—CH₂—CH₂ | H | H | CH₃ | CH | |
| 492 | 4-F—C₆H₄—CH=CH—CH₂—CH₂ | H | H | CH₃ | N | |
| 493 | t-C₄H₉O—CO—CH₂ | H | H | CH₃ | CH | |
| 494 | t-C₄H₉O—CO—CH₂ | H | H | CH₃ | N | |
| 495 | t-C₄H₉O—CO—(CH₂)₃ | H | H | CH₃ | CH | |
| 496 | t-C₄H₉O—CO—(CH₂)₃ | H | H | CH₃ | N | |
| 497 | Cl—CH=CH—CH₂ | H | H | CH₃ | CH | oil (E) |
| 498 | Cl—CH=CH—CH₂ | H | H | CH₃ | N | oil (E) |
| 499 | C₂H₅ | 6-OC₂H₅ | H | CH₃ | CH | |
| 500 | C₂H₅ | 6-OC₂H₅ | H | CH₃ | N | |
| 501 | CH₃—C(CH₃)₂ | H | H | CH₃ | CH | oil (E) |
| 502 | CH₃—C(CH₃)₂ | H | H | CH₃ | N | 83-85 (E) |
| 503 | CH₃—CH(CH₃)—CH₂ | H | H | CH₃ | CH | oil (E) |
| 504 | CH₃—CH(CH₃)—CH₂ | H | H | CH₃ | N | 70-72 (E) |
| 505 | CH₂=C(CH₃)—CH₂ | H | H | CH₃ | CH | oil (E) |
| 506 | CH₂=C(CH₃)—CH₂ | H | H | CH₃ | N | 64-65 (E) |
| 507 | CH₃—CH(CH₃)—CH₂—CH₂ | H | H | CH₃ | CH | oil (E) |
| 508 | CH₃—CH(CH₃)—CH₂—CH₂ | H | H | CH₃ | N | oil (E) |
| 509 | CH₃—(CH₂)₄ | H | H | CH₃ | CH | |
| 510 | CH₃—(CH₂)₄ | H | H | CH₃ | N | |
| 511 | 2-F—C₆H₄—CH₂ | H | H | CH₃ | CH | |
| 512 | 2-F—C₆H₄—CH₂ | H | H | CH₃ | N | |
| 513 | 3-F—C₆H₄—CH₂ | H | H | CH₃ | CH | |
| 514 | 3-F—C₆H₄—CH₂ | H | H | CH₃ | N | |
| 515 | 2-Cl—C₆H₄—CH₂ | H | H | CH₃ | CH | |
| 516 | 2-Cl—C₆H₄—CH₂ | H | H | CH₃ | N | |
| 517 | 3,4-Cl₂—C₆H₃—CH₂ | H | H | CH₃ | CH | |
| 518 | 3,4-Cl₂—C₆H₃—CH₂ | H | H | CH₃ | N | |
| 519 | 2,6-Cl₂—C₆H₃—CH₂ | H | H | CH₃ | CH | |
| 520 | 2,6-Cl₂—C₆H₃—CH₂ | H | H | CH₃ | N | |
| 521 | C₆H₅—CH₂—CH₂ | H | H | CH₃ | CH | |
| 522 | C₆H₅—CH₂—CH₂ | H | H | CH₃ | N | |
| 523 | C₆H₅—CH=CH—CH₂—CH₂ | H | H | CH₃ | CH | |
| 524 | C₆H₅—CH=CH—CH₂—CH₂ | H | H | CH₃ | N | |
| 525 | 4-Cl—C₆H₄—CH₂—CH=CH—CH₂ | H | H | CH₃ | CH | |
| 526 | 4-Cl—C₆H₄—CH₂—CH=CH—CH₂ | H | H | CH₃ | N | |
| 527 | 4-CF₃—C₆H₄—CH₂—CH=CH—CH₂ | H | H | CH₃ | CH | |
| 528 | 4-CF₃—C₆H₄—CH₂—CH=CH—CH₂ | H | H | CH₃ | N | |
| 529 | CH₃ | H | H | C₆H₅ | CH | |
| 530 | CH₃ | H | H | C₆H₅ | N | |
| 531 | C₂H₅ | H | H | C₆H₅ | CH | |
| 532 | C₂H₅ | H | H | C₆H₅ | N | |
| 533 | CH₃—CH₂—CH₂ | H | H | C₆H₅ | CH | |
| 534 | CH₃—CH₂—CH₂ | H | H | C₆H₅ | N | |
| 535 | CH₃—(CH₂)₅ | H | H | C₆H₅ | CH | |
| 536 | CH₃—(CH₂)₅ | H | H | C₆H₅ | N | |
| 537 | C₆H₅—CH₂ | H | H | C₆H₅ | CH | |

TABLE 2-continued

Compounds of the general formula Ib (3-position of the oxime ether).
The configuration statement relates to the
methyl β-methoxyacrylate group or the methyl glyoxylate O-methyloxime group.

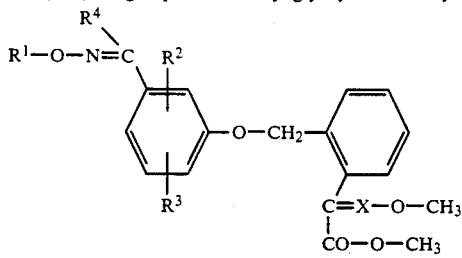

Ib

| Comp. no. | R¹ | R² | R³ | R⁴ | X | mp. (°C.) |
|---|---|---|---|---|---|---|
| 538 | C₆H₅—CH₂ | H | H | C₆H₅ | N | |

TABLE 3

Compounds of the formula Ic (4-position of the oxime ether).
The configuration statement relates to the methyl
β-methoxyacrylate group or the methyl glyoxylate O-methyloxime group.

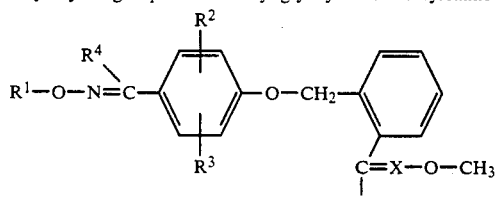

Ic

| Comp. no. | R¹ | R² | R³ | R⁴ | X | mp. (°C.) |
|---|---|---|---|---|---|---|
| 149 | CH₃— | H | H | H | CH | 84–86 (E) |
| 150 | CH₃— | H | H | H | N | 88–91 (E) |
| 151 | CH₃— | 2-Cl | H | H | CH | |
| 152 | CH₃— | 2-Cl | H | H | N | |
| 153 | CH₃— | 2-CH₃ | H | H | CH | |
| 154 | CH₃— | 2-CH₃ | H | H | N | |
| 155 | CH₃— | 2-OCH₃ | H | H | CH | oil (E) |
| 156 | CH₃— | 2-OCH₃ | H | H | N | 105–107 (E) |
| 157 | CH₃— | 3-Cl | H | H | CH | |
| 158 | CH₃— | 3-Cl | H | H | N | |
| 159 | CH₃— | 3-CH₃ | H | H | CH | |
| 160 | CH₃— | 3-CH₃ | H | H | N | |
| 161 | CH₃ | 3-OCH₃ | H | H | CH | |
| 162 | CH₃— | 3-OCH₃ | H | H | N | |
| 163 | CH₃ | 2-Cl | 6-Cl | H | CH | |
| 164 | CH₃ | 2-Cl | 6-Cl | H | N | |
| 165 | CH₃—CH₂— | H | H | H | CH | 108–110 (E) |
| 166 | CH₃—CH₂ | H | H | H | N | 106–108 (E) |
| 167 | CH₃—CH₂— | 2-Cl | H | H | CH | |
| 168 | CH₃—CH₂— | 2-Cl | H | H | N | |
| 169 | CH₃—CH₂— | 2-CH₃ | H | H | CH | |
| 170 | CH₃—CH₂— | 2-CH₃ | H | H | N | |
| 171 | CH₃—CH₂— | 2-OCH₃ | H | H | CH | |
| 172 | CH₃—CH₂— | 2-OCH₃ | H | H | N | |
| 173 | CH₃—CH₂— | 3-Cl | H | H | CH | |
| 174 | CH₃—CH₂— | 3-Cl | H | H | N | |
| 175 | CH₃—CH₂— | 3-CH₃ | H | H | CH | |
| 176 | CH₃—CH₂— | 3-CH₃ | H | H | N | |
| 177 | CH₃—CH₂— | 3-OCH₃ | H | H | CH | |
| 178 | CH₃—CH₂— | 3-OCH₃ | H | H | N | |
| 179 | CH₃—CH₂— | 2-Cl | 6-Cl | H | CH | |
| 180 | CH₃—CH₂— | 2-Cl | 6-Cl | H | N | |
| 181 | CH₃—CH₂—CH₂— | H | H | H | CH | |
| 182 | CH₃—CH₂—CH₂— | H | H | H | N | |
| 183 | CH₂=CH—CH₂— | H | H | H | CH | 103–105 (E) |
| 184 | CH₂=CH—CH₂— | H | H | H | N | 82–84 (E) |
| 185 | CH₃—CH(CH₃)— | H | H | H | CH | |
| 186 | CH₃—CH(CH₃)— | H | H | H | N | |
| 187 | HC≡C—CH₂— | H | H | H | CH | |
| 188 | HC≡C—CH₂— | H | H | H | N | |
| 189 | cyclo-C₃H₅—CH₂— | H | H | H | CH | |
| 190 | cyclo-C₃H₅—CH₂— | H | H | H | N | |
| 191 | CH₃—CH₂—CH₂—CH₂— | H | H | H | CH | |
| 192 | CH₃—CH₂—CH₂—CH₂— | H | H | H | N | |
| 193 | CH₃—CH=CH—CH₂— | H | H | H | CH | |

TABLE 3-continued

Compounds of the formula Ic (4-position of the oxime ether).
The configuration statement relates to the methyl
β-methoxyacrylate group or the methyl glyoxylate O-methyloxime group.

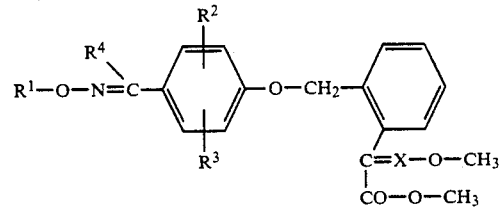

Ic

| Comp. no. | R¹ | R² | R³ | R⁴ | X | mp. (°C.) |
|---|---|---|---|---|---|---|
| 194 | $CH_3-CH=CH-CH_2-$ | H | H | H | N | |
| 195 | $CH_3-(CH_2)_5-$ | H | H | H | CH | 62-63 (E) |
| 196 | $CH_3-(CH_2)_5-$ | H | H | H | N | 72-73 (E) |
| 197 | cyclo-$C_6H_{11}$ | H | H | H | CH | |
| 198 | cyclo-$C_6H_{11}-$ | H | H | H | N | |
| 199 | $C_6H_5-CH_2-$ | H | H | H | CH | 103-105 (E) |
| 200 | $C_6H_5-CH_2-$ | H | H | H | N | 151-153 (E) |
| 201 | 4-Cl-$C_6H_4-CH_2-$ | H | H | H | CH | |
| 202 | 4-Cl-$C_6H_4-CH_2-$ | H | H | H | N | |
| 203 | 3-$CF_3-C_6H_4-CH_2-$ | H | H | H | CH | |
| 204 | 3-$CF_3-C_6H_4-CH_2-$ | H | H | H | N | |
| 205 | 4-Cl-$C_6H_4-CH_2-CH_2-$ | H | H | H | CH | |
| 206 | 4-Cl-$C_6H_4-CH_2-CH_2-$ | H | H | H | N | |
| 207 | $C_6H_5-CH_2-CH_2-CH_2-$ | H | H | H | CH | |
| 208 | $C_6H_5-CH_2-CH_2-CH_2-$ | H | H | H | N | |
| 209 | $C_6H_5-(CH_2)_4-$ | H | H | H | CH | |
| 210 | $C_6H_5-(CH_2)_4-$ | H | H | H | N | |
| 211 | $C_6H_5-CH_2-CH=CH-CH_2-$ | H | H | H | CH | |
| 212 | $C_6H_5-CH_2-CH=CH-CH_2-$ | H | H | H | N | |
| 213 | 4-F-$C_6H_4-CH=CH-CH_2-CH_2-$ | H | H | H | CH | |
| 214 | 4-F-$C_6H_4-CH=CH-CH_2-CH_2-$ | H | H | H | N | |
| 215 | t-$C_4H_9O-CO-CH_2-$ | H | H | H | CH | |
| 216 | t-$C_4H_9O-CO-CH_2-$ | H | H | H | N | |
| 217 | t-$C_4H_9O-CO-(CH_2)_3-$ | H | H | H | CH | |
| 218 | t-$C_4H_9O-CO-(CH_2)_3-$ | H | H | H | N | |
| 219 | Cl-CH=CH-$CH_2-$ | H | H | H | CH | oil (E) |
| 220 | Cl-CH=CH-$CH_2-$ | H | H | H | N | 95-97 (E) |
| 281 | $C_2H_5$ | 6-$OC_2H_5$ | H | H | CH | |
| 282 | $C_2H_5$ | 6-$OC_2H_5$ | H | H | N | |
| 283 | $CH_3-C(CH_3)_2-$ | H | H | H | CH | |
| 284 | $CH_3-C(CH_3)_2-$ | H | H | H | N | |
| 285 | $CH_3-CH(CH_3)-CH_2-$ | H | H | H | CH | |
| 286 | $CH_3-CH(CH_3)-CH_2-$ | H | H | H | N | |
| 287 | $CH_2=C(CH_3)-CH_2$ | H | H | H | CH | 100-102 (E) |
| 288 | $CH_2=C(CH_3)-CH_2$ | H | H | H | N | 95-96 (E) |
| 289 | $CH_3-CH(CH_3)-CH_2-CH_2-$ | H | H | H | CH | |
| 290 | $CH_3-CH(CH_3)-CH_2-CH_2-$ | H | H | H | N | |
| 291 | $CH_3-(CH_2)_4-$ | H | H | H | CH | |
| 292 | $CH_3-(CH_2)_4-$ | H | H | H | N | oil (E) |
| 293 | 2-F-$C_6H_4-CH_2-$ | H | H | H | CH | |
| 294 | 2-F-$C_6H_4-CH_2-$ | H | H | H | N | |
| 295 | 3-F-$C_6H_4-CH_2-$ | H | H | H | CH | |
| 296 | 3-F-$C_6H_4-CH_2-$ | H | H | H | N | |
| 297 | 2-Cl-$C_6H_4-CH_2-$ | H | H | H | CH | |
| 298 | 2-Cl-$C_6H_4-CH_2-$ | H | H | H | N | |
| 299 | 3,4-$Cl_2-C_6H_3-CH_2-$ | H | H | H | CH | |
| 300 | 3,4-$Cl_2-C_6H_3-CH_2-$ | H | H | H | N | |
| 301 | 2,6-$Cl_2-C_6H_3-CH_2-$ | H | H | H | CH | |
| 302 | 2,6-$Cl_2-C_6H_3-CH_2-$ | H | H | H | N | |
| 303 | $C_6H_5-CH_2-CH_2-$ | H | H | H | CH | |
| 304 | $C_6H_5-CH_2-CH_2-$ | H | H | H | N | |
| 305 | $C_6H_5-CH=CH-CH_2-CH_2-$ | H | H | H | CH | |
| 306 | $C_6H_5-CH=CH-CH_2-CH_2-$ | H | H | H | N | |
| 307 | 4-Cl-$C_6H_4-CH_2-CH=CH-CH_2-$ | H | H | H | CH | |
| 308 | 4-Cl-$C_6H_4-CH_2-CH=CH-CH_2-$ | H | H | H | N | |
| 309 | 4-$CF_3-C_6H_4-CH_2-CH=CH-CH_2-$ | H | H | H | CH | |
| 310 | 4-$CF_3-C_6H_4-CH_2-CH=CH-CH_2-$ | H | H | H | N | |
| 539 | $CH_3$ | H | H | $CH_3$ | CH | oil (E) |
| 540 | $CH_3$ | H | H | $CH_3$ | N | 99-100 (E) |
| 541 | $CH_3$ | 2-Cl | H | $CH_3$ | CH | |
| 542 | $CH_3$ | 2-Cl | H | $CH_3$ | N | |
| 543 | $CH_3$ | 2-$CH_3$ | H | $CH_3$ | CH | |
| 544 | $CH_3$ | 2-$CH_3$ | H | $CH_3$ | N | |
| 545 | $CH_3$ | 2-$OCH_3$ | H | $CH_3$ | CH | |
| 546 | $CH_3$ | 2-$OCH_3$ | H | $CH_3$ | N | |
| 547 | $CH_3$ | 3-Cl | H | $CH_3$ | CH | |
| 548 | $CH_3$ | 3-Cl | H | $CH_3$ | N | |
| 549 | $CH_3$ | 3-$CH_3$ | H | $CH_3$ | CH | |

TABLE 3-continued

Compounds of the formula Ic (4-position of the oxime ether). The configuration statement relates to the methyl β-methoxyacrylate group or the methyl glyoxylate O-methyloxime group.

$$R^1-O-N=C(R^4)-\text{[phenyl-}R^2,R^3\text{]}-O-CH_2-\text{[phenyl-}C(=X)-O-CH_3, CO-O-CH_3\text{]} \quad \text{Ic}$$

| Comp. no. | $R^1$ | $R^2$ | $R^3$ | $R^4$ | X | mp. (°C.) |
|---|---|---|---|---|---|---|
| 550 | $CH_3$ | 3-$CH_3$ | H | $CH_3$ | N | |
| 551 | $CH_3$ | 3-$OCH_3$ | H | $CH_3$ | CH | |
| 552 | $CH_3$ | 3-$OCH_3$ | H | $CH_3$ | N | |
| 553 | $CH_3$ | 2-Cl | 6-Cl | $CH_3$ | CH | |
| 554 | $CH_3$ | 2-Cl | 6-Cl | $CH_3$ | N | |
| 555 | $CH_3-CH_2$ | H | H | $CH_3$ | CH | 71–73 (E) |
| 556 | $CH_3-CH_2$ | H | H | $CH_3$ | N | 79–80 (E) |
| 557 | $CH_3-CH_2$ | 2-Cl | H | $CH_3$ | CH | |
| 558 | $CH_3-CH_2$ | 2-Cl | H | $CH_3$ | N | |
| 559 | $CH_3-CH_2$ | 2-$CH_3$ | H | $CH_3$ | CH | |
| 560 | $CH_3-CH_2$ | 2-$CH_3$ | H | $CH_3$ | N | |
| 561 | $CH_3-CH_2$ | 2-$OCH_3$ | H | $CH_3$ | CH | |
| 562 | $CH_3-CH_2$ | 2-$OCH_3$ | H | $CH_3$ | N | |
| 563 | $CH_3-CH_2$ | 3-Cl | H | $CH_3$ | CH | |
| 564 | $CH_3-CH_2$ | 3-Cl | H | $CH_3$ | N | |
| 565 | $CH_3-CH_2$ | 3-$CH_3$ | H | $CH_3$ | CH | |
| 566 | $CH_3-CH_2$ | 3-$CH_3$ | H | $CH_3$ | N | |
| 567 | $CH_3-CH_2$ | 3-$OCH_3$ | H | $CH_3$ | CH | |
| 568 | $CH_3-CH_2$ | 3-$OCH_3$ | H | $CH_3$ | N | |
| 569 | $CH_3-CH_2$ | 2-Cl | 6-Cl | $CH_3$ | CH | |
| 570 | $CH_3-CH_2$ | 2-Cl | 6-Cl | $CH_3$ | N | |
| 571 | $CH_3-CH_2-CH_2$ | H | H | $CH_3$ | CH | 97–99 (E) |
| 572 | $CH_3-CH_2-CH_2$ | H | H | $CH_3$ | N | 100–101 (E) |
| 573 | $CH_2=CH-CH_2$ | H | H | $CH_3$ | CH | 90–92 (E) |
| 574 | $CH_2=CH-CH_2$ | H | H | $CH_3$ | N | 107–108 (E) |
| 575 | $CH_3-CH(CH_3)$ | H | H | $CH_3$ | CH | 120–123 (E) |
| 576 | $CH_3-CH(CH_3)$ | H | H | $CH_3$ | N | 109–110 (E) |
| 577 | $HC\equiv C-CH_2$ | H | H | $CH_3$ | CH | |
| 578 | $HC\equiv C-CH_2$ | H | H | $CH_3$ | N | |
| 579 | cyclo-$C_3H_5-CH_2$ | H | H | $CH_3$ | CH | |
| 580 | cyclo-$C_3H_5-CH_2$ | H | H | $CH_3$ | N | |
| 581 | $CH_3-CH_2-CH_2-CH_2$ | H | H | $CH_3$ | CH | 64–66 (E) |
| 582 | $CH_3-CH_2-CH_2-CH_2$ | H | H | $CH_3$ | N | oil (E) |
| 583 | $CH_3-CH=CH-CH_2$ | H | H | $CH_3$ | CH | oil (E) |
| 584 | $CH_3-CH=CH-CH_2$ | H | H | $CH_3$ | N | 100–103 (E) |
| 585 | $CH_3-(CH_2)_5$ | H | H | $CH_3$ | CH | 65–67 (E) |
| 586 | $CH_3-(CH_2)_5$ | H | H | $CH_3$ | N | 60–63 (E) |
| 587 | cyclo-$C_6H_{11}$ | H | H | $CH_3$ | CH | |
| 588 | cyclo-$C_6H_{11}$ | H | H | $CH_3$ | N | |
| 589 | $C_6H_5-CH_2$ | H | H | $CH_3$ | CH | 110–112 (E) |
| 590 | $C_6H_5-CH_2$ | H | H | $CH_3$ | N | 104–106 (E) |
| 591 | 4-Cl—$C_6H_4-CH_2$ | H | H | $CH_3$ | CH | |
| 592 | 4-Cl—$C_6H_4-CH_2$ | H | H | $CH_3$ | N | |
| 593 | 3-$CF_3$—$C_6H_4-CH_2$ | H | H | $CH_3$ | CH | |
| 594 | 3-$CF_3$—$C_6H_4-CH_2$ | H | H | $CH_3$ | N | |
| 595 | 4-Cl—$C_6H_4-CH_2-CH_2$ | H | H | $CH_3$ | CH | |
| 596 | 4-Cl—$C_6H_4-CH_2-CH_2$ | H | H | $CH_3$ | N | |
| 597 | $C_6H_5-CH_2-CH_2-CH_2$ | H | H | $CH_3$ | CH | |
| 598 | $C_6H_5-CH_2-CH_2-CH_2$ | H | H | $CH_3$ | N | |
| 599 | $C_6H_5-(CH_2)_4$ | H | H | $CH_3$ | CH | |
| 600 | $C_6H_5-(CH_2)_4$ | H | H | $CH_3$ | N | |
| 601 | $C_6H_5-CH_2-CH=CH-CH_2$ | H | H | $CH_3$ | CH | |
| 602 | $C_6H_5-CH_2-CH=CH-CH_2$ | H | H | $CH_3$ | N | |
| 603 | 4-F—$C_6H_4-CH=CH-CH_2-CH_2$ | H | H | $CH_3$ | CH | |
| 604 | 4-F—$C_6H_4-CH=CH-CH_2-CH_2$ | H | H | $CH_3$ | N | |
| 605 | t-$C_4H_9O-CO-CH_2$ | H | H | $CH_3$ | CH | |
| 606 | t-$C_4H_9O-CO-CH_2$ | H | H | $CH_3$ | N | |
| 607 | t-$C_4H_9O-CO-(CH_2)_3$ | H | H | $CH_3$ | CH | |
| 608 | t-$C_4H_9O-CO-(CH_2)_3$ | H | H | $CH_3$ | N | |
| 609 | Cl—CH=CH—$CH_2$ | H | H | $CH_3$ | CH | 98–100 (E) |
| 610 | Cl—CH=CH—$CH_2$ | H | H | $CH_3$ | N | 105–107 (E) |
| 611 | $C_2H_5$ | 6-$OC_2H_5$ | H | $CH_3$ | CH | |
| 612 | $C_2H_5$ | 6-$OC_2H_5$ | H | $CH_3$ | N | |
| 613 | $CH_3-C(CH_3)_2$ | H | H | $CH_3$ | CH | 88–90 (E) |
| 614 | $CH_3-C(CH_3)_2$ | H | H | $CH_3$ | N | 75–78 (E) |
| 615 | $CH_3-CH(CH_3)-CH_2$ | H | H | $CH_3$ | CH | 85–87 (E) |
| 616 | $CH_3-CH(CH_3)-CH_2$ | H | H | $CH_3$ | N | 79–81 (E) |
| 617 | $CH_2=C(CH_3)-CH_2$ | H | H | $CH_3$ | CH | 94–96 (E) |

TABLE 3-continued

Compounds of the formula Ic (4-position of the oxime ether).
The configuration statement relates to the methyl
β-methoxyacrylate group or the methyl glyoxylate O-methyloxime group.

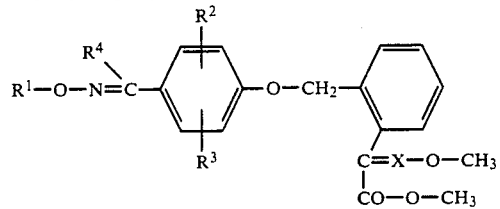

Ic

| Comp. no. | R¹ | R² | R³ | R⁴ | X | mp. (°C.) |
|---|---|---|---|---|---|---|
| 618 | CH₂=C(CH₃)—CH₂ | H | H | CH₃ | N | 88–89 (E) |
| 619 | CH₃—CH(CH₃)—CH₂—CH₂ | H | H | CH₃ | CH | 46–48 (E) |
| 620 | CH₃—CH(CH₃)—CH₂—CH₂ | H | H | CH₃ | N | oil (E) |
| 621 | CH₃—(CH₂)₄ | H | H | CH₃ | CH | |
| 622 | CH₃—(CH₂)₄ | H | H | CH₃ | N | |
| 623 | 2-F—C₆H₄—CH₂ | H | H | CH₃ | CH | |
| 624 | 2-F—C₆H₄—CH₂ | H | H | CH₃ | N | |
| 625 | 3-F—C₆H₄—CH₂ | H | H | CH₃ | CH | |
| 626 | 3-F—C₆H₄—CH₂ | H | H | CH₃ | N | |
| 627 | 2-Cl—C₆H₄—CH₂ | H | H | CH₃ | CH | |
| 628 | 2-Cl—C₆H₄—CH₂ | H | H | CH₃ | N | |
| 629 | 3,4-Cl₂—C₆H₃—CH₂ | H | H | CH₃ | CH | |
| 630 | 3,4-Cl₂—C₆H₃—CH₂ | H | H | CH₃ | N | |
| 631 | 2,6-Cl₂—C₆H₃—CH₂ | H | H | CH₃ | CH | |
| 632 | 2,6-Cl₂—C₆H₃—CH₂ | H | H | CH₃ | N | |
| 633 | C₆H₅—CH₂—CH₂ | H | H | CH₃ | CH | |
| 634 | C₆H₅—CH₂—CH₂ | H | H | CH₃ | N | |
| 635 | C₆H₅—CH=CH—CH₂—CH₂ | H | H | CH₃ | CH | |
| 636 | C₆H₅—CH=CH—CH₂—CH₂ | H | H | CH₃ | N | |
| 637 | 4-Cl—C₆H₄—CH₂—CH=CH—CH₂ | H | H | CH₃ | CH | |
| 638 | 4-Cl—C₆H₄—CH₂—CH=CH—CH₂ | H | H | CH₃ | N | |
| 639 | 4-CF₃—C₆H₄—CH₂—CH=CH—CH₂ | H | H | CH₃ | CH | |
| 640 | 4-CF₃—C₆H₄—CH₂—CH=CH—CH₂ | H | H | CH₃ | N | |
| 641 | CH₃ | H | H | C₆H₅ | CH | |
| 642 | CH₃ | H | H | C₆H₅ | N | |
| 643 | C₂H₅ | H | H | C₆H₅ | CH | |
| 644 | C₂H₅ | H | H | C₆H₅ | N | |
| 645 | CH₃—CH₂—CH₂ | H | H | C₆H₅ | CH | |
| 646 | CH₃—CH₂—CH₂ | H | H | C₆H₅ | N | |
| 647 | CH₃—(CH₂)₅ | H | H | C₆H₅ | CH | |
| 648 | CH₃—(CH₂)₅ | H | H | C₆H₅ | N | |
| 649 | C₆H₅—CH₂ | H | H | C₆H₅ | CH | |
| 650 | C₆H₅—CH₂ | H | H | C₆H₅ | N | |

Table 4

¹H-NMR data of selected compounds from Tables 1, 2 and 3. The chemical shift (δ) is given in ppm relative to tetramethylsilane. The solvent employed is CDCl₃.

Compound no. 1

3.67 (s, 3H); 3.77 (s, 3H); 3.93 (s, 3H); 4.98 (s, 2H); 6.81-7.81 (m, 8H); 7.57 (s, 1H); 8.49 (s, 1H).

Compound no. 2

3.40 (s, 3H); 3.95 (s, 3H); 4.05 (s, 3H); 4.95 (s, 2H); 6.80-7.85 (m, 8H); 8.45 (s, 1H).

Compound no. 23

1.31 (t, 3H); 3.67 (s, 3H); 3.79 (s, 3H); 4.20 (q, 2H); 4.97 (s, 2H); 6.83-7.83 (m, 8H); 7.59 (s, 1H); 8.51 (s, 1H).

Compound no. 24

1.30 (t, 3H); 3.80 (s, 3H); 4.05 (s, 3H); 4.20 (q, 2H); 4.95 (s, 2H); 6.80-7.85 (m, 8H); 8.45 (s, 1H).

Compound no. 85

3.65 (s, 3H); 3.68 (s, 3H); 3.92 (s, 3H); 4.95 (s, 2H); 6.85-7.52 (m, 8H); 7.55 (s, 1H); 7.98 (s, 1H).

Compound no. 97

1.28 (t, 3H); 3.68 (s, 3H); 3.73 (s, 3H); 4.20 (q, 2H); 4.97 (s, 2H); 6.85-7.53 (m, 8H); 7.57 (s, 1H); 8.00 (s, 1H).

Compound no. 149

3.68 (s, 3H); 3.77 (s, 3H); 3.92 (s, 3H); 4.98 (s, 2H); 6.87-7.53 (m, 8H); 7.59 (s, 1H); 7.98 (s, 1H).

Compound no. 165

1.31 (t, 3H); 3.69 (s, 3H); 3.80 (s, 3H); 4.20 (q, 2H); 5.00 (s, 2H); 6.87-7.53 (m, 8H); 7.60 (s, 1H); 8.00 (s, 1H).

Compound no. 447

1.32 (t, 3H); 2.18 (s, 3H); 3.68 (s, 3H); 3.77 (s, 3H); 4.22 (q, 2H); 4.97 (s, 2H); 6.83-7.53 (m, 8H); 7.55 (s, 1H).

Compound no. 488

1.32 (t, 3H); 2.17 (s, 3H); 3.82 (s, 3H); 4.00 (s, 3H); 4.23 (q, 4H); 4.97 (s, 2H); 6.83-7.57 (m, 8H).

Compound no. 470

0.95 (t, 3H); 1.43 (m, 2H); 1.70 (m, 2H); 2.18 (s, 3H); 3.83 (s, 3H); 4.00 (s, 3H); 4.17 (t, 2H); 4.97 (s, 2H); 6.82-7.55 (m, 8).

Compound no. 474

0.87 (t, 3H); 1.32 (m, 6H); 1.70 (m, 2H); 2.18 (s, 3H); 3.83 (s, 3H); 4.02 (s, 3H); 4.17 (t, 2H); 4.95 (s, 2H); 6.83-7.57 (m, 8H).

Compound no. 478

2.22 (s, 3H); 3.78 (s, 3H); 4.00 (s, 3H); 4.97 (s, 2H); 5.23 (s, 2H); 6.82-7.53 (m, 8H).

Compound no. 556

1.33 (t, 3H); 2.20 (s, 3H); 3.83 (s, 3H); 4.02 (s, 3H); 4.22 (q, 2H); 4.97 (s, 2H); 6.85-7.60 (m, 8H).

Compound no. 582

0.97 (t, 3H); 1.40 (m, 2H); 1.68 (m, 2H); 2.17 (s, 3H); 3.83 (s, 3H); 4.00 (s, 3H); 4.15 (t, 2H); 4.95 (s, 2H); 6.82-7.57 (m, 8H).

Compound no. 586

0.88 (t, 3H); 1.32 (m, 6H); 1.70 (m, 2H); 2.18 (s, 3H); 3.83 (s, 3H); 4.01 (s, 3H); 4.15 (t, 2H); 4.95 (s, 2H); 6.83-7.57 (m, 8H).

Compound no. 590

2.22 (s, 3H); 3.83 (s, 3H); 4.02 (s, 3H); 4.95 (s, 2H); 5.22 (s, 2H); 6.82-7.57 (m, 8H).

Generally speaking, the novel compounds are extremely effective on a broad spectrum of phytopathogenic fungi, in particular those from the Ascomycetes and Basidiomycetes classes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:
Erysiphe graminis in cereals,
Erysiphe cichoracearum and Sphaerotheca fuliginea in cucurbits,
Podosphaera leucotricha in apples,
Uncinula necator in vines,
Puccinia species in cereals,
Rhizoctonia species in cotton and lawns,
Ustilago species in cereals and sugar cane,
Venturia inaequalis (scab) in apples,
Helminthosporium species in cereals,
Septoria nodorum in wheat,
Botrytis cinerea (gray mold) in strawberries and grapes,
Cercospora arachidicola in groundnuts,
Pseudocercosporella herpotrichoides in wheat and barley,
Pyricularia oryzae in rice,
Phytophthora infestans in potatoes and tomatoes,
Fusarium and Verticillium species in various plants,
Plasmopara viticola in grapes,
Alternaria species in fruit and vegetables.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all event ensure a fine and uniform distribution of the active ingredient. The formulations are produced in known manner, for example by extending the active ingredient with solvents and/or carriers, with or without the use of emulsifier and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicidal agents generally contain from 0.1 to 95, and preferably from 0.5 to 90, wt % of active ingredient. The application rates are from 0.02 to 3 kg or more of active ingredient per hectare, depending on the type of effect desired. The novel compounds may also be used for protecting materials, for example against Paecilomyces variotii.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 85 is mixed with 10 parts by weight of N-methyl-α-pyrrolidone. A mixture is obtained which is suitable for application in the form of very fine drops.

II. 20 parts by weight of compound no. 97 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 447 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 470 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 149 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 165 is intimately mixed with 97 parts by weight of particulate kaolin. A dust is obtained containing 3% by weight of the active ingredient.

VII. 30 parts by weight of compound no. 590 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 448 is intimately mixed with 10 parts by weight of the sodium salt of a phenosulfonic acid-urea-formaldehye condensate, 2 parts of silica gel and 48 parts of water to give a stable aqueous dispersion. Dilution in water gives an aqueous dispersion.

IX. 20 parts by weight of compound no. 85 is intimately mixed with 2 parts by weight of the calcium salt of dodecylbenzenesulfonic acid, 8 parts by weight of a fatty alcohol polyglycol ether, 2 parts by weight of the sodium salt of a phenosulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixtue with other fungicides frequently results in an increase in the fungicidal spectrum.

USE EXAMPLES

The comparative agent which was employed was methyl 2-(phenoxymethyl)phenylglyoxylate O-methyloxime (A) disclosed in EP 253,213.

USE EXAMPLE 1

Action on wheat brown rust

Leaves of pot-grown wheat seedlings of the "Kanzler" variety were dusted with spores of brown rust (Puccinia recondita). The pots were then placed for 24 hours at 20° to 22° C. in a high-humidity (90–95%) chamber. During this period the spores germinated and the germ tubes penetrated the leaf tissue. The infected plants were then sprayed to runoff with aqueous liquors containing (dry basis) 80% of active ingredient and 20% of emulsifier. After the sprayed-on layer had dried, the plants were set up in the greenhouse at 20° to 22° C. and a relative humidity of 65 to 70%. The extent of rust fungus spread on the leaves was assessed after 8 days.

The results show that active ingredients 85 and 97, applied as 0.025 wt % spray liquors, have a better fungicidal action (100%) than prior art comparative agent A (35%).

In another experiment, it was found that active ingredients 111, 112, 113, 119, 123, 195, 220, 262, 265, 266, 273, 275, 447 and 470, applied as 0.025 wt % spray liquors, have a better fungicidal action (95%) than prior art comparative agent A (35%).

USE EXAMPLE 2

Action on Plasmopara viticola

Leaves of potted vines of the Müller-Thurgau variety were sprayed with aqueous liquors containing (dry basis) 80% of active ingredient and 20% of emulsifier. To assess the duration of action, the plants were set up, after the sprayed-on layer had dried, for 8 days in the greenhouse. Then the leaves were infected with a zoospore suspension of Plasmopara viticola. The plants were first placed for 48 hours in a water vapor-saturated chamber at 24° C. and then in a greenhouse for 5 days at from 20° to 30° C. To accelerate and intensify the sporangiophore discharge, the plants were then again placed in the moist chamber for 16 hours. The extent of fungus attack was then assessed on the undersides of the leaves.

The results show that active ingredients 85, 97, 149 and 165, applied as 0.0125% spray liquors, have a better fungicidal action (100%) than prior art comparative agent A (50%).

In a further experiment, it was found that active ingredients 86, 88, 111, 113, 114, 119, 120, 123, 124, 127, 150, 155, 183, 184, 199, 219, 220, 263, 265, 267, 273, 275, 277, 287, 288, 447 and 448, applied as 0.0125% spray liquors, have a better fungicidal action (95%) than prior art comparative agent A (50%).

We claim:

1. A substituted oxime ether of the general formula I

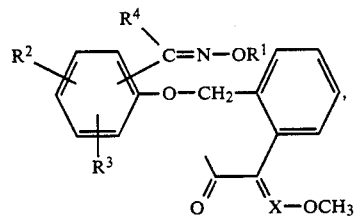

where $R^1$ is $C_1$–$C_6$-alkyl, $C_3$–$C_6$-alkenyl, $C_3$–$C_4$-alkynyl, $C_1$–$C_6$-haloalkyl, $C_3$–$C_6$-haloalkenyl, $C_1$–$C_4$-alkoxy-$C_1$–$C_6$-alkyl, $C_3$–$C_6$-cycloalkyl, $C_3$–$C_6$-cycloalkyl-$C_1$–$C_4$-alkyl, cyano-$C_1$–$C_6$-alkyl, $C_1$–$C_6$-alkoxycarbonyl-$C_1$–$C_6$-alkyl, aryl-$C_1$–$C_6$-alkyl, pyridyl-$C_1$–$C_6$-alkyl, thienyl-$C_1$–$C_6$-alkyl, aryl-$C_3$–$C_6$-alkenyl or aryloxy-$C_1$–$C_6$-alkyl, it being possible for the aromatic, pyridyl, or thienyl ring to be substituted by one or more of the following: $C_1$–$C_4$-alkyl, $C_1$–$C_2$-haloalkyl, $C_3$–$C_6$-cycloalkyl, $C_1$–$C_4$-alkoxy; $C_1$–$C_2$-haloalkoxy, halogen, aryl or aryloxy, $R^2$ and $R^3$ are identical or different and are hydrogen, $C_1$–$C_4$-alkyl, $C_1$–$C_2$-haloalkyl, $C_1$–$C_4$-alkoxy, $C_1$–$C_2$-haloalkoxy, halogen, cyano or nitro, $R^2$ is hydrogen, $C_1$–$C_6$-alkyl or aryl, it being possible for the aromatic ring to be substituted by one or more of the following: $C_1$–$C_4$-alkyl, $C_1$–$C_2$-haloalkyl, $C_1$–$C_4$-alkoxy, $C_1$–$C_2$-haloalkoxy, halogen, cyano or nitro, and x is CH or N.

2. A fungicide containing an inert carrier and a fungicidally effective amount of a substituted oxime ether of the general formula I

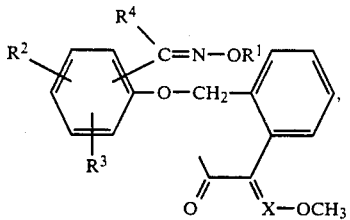

where $R^1$ is $C_1$–$C_6$-alkyl, $C_3$–$C_6$-alkenyl, $C_3$–$C_4$-alkynyl, $C_1$–$C_6$-haloalkyl, $C_3$–$C_6$-haloalkenyl, $C_1$–$C_4$-alkoxy-$C_1$–$C_6$-alkyl, $C_3$–$C_6$-cycloalkyl, $C_3$–$C_6$-cycloalkyl-$C_1$–$C_4$-alkyl, cyano-$C_1$–$C_6$-alkyl, $C_1$–$C_6$-alkoxycarbonyl-$C_1$–$C_6$-alkyl, aryl-$C_1$–$C_6$-alkyl, pyridyl-$C_1$–$C_6$-alkyl, thienyl-$C_1$–$C_6$-alkyl, aryl-$C_3$–$C_6$-alkenyl or aryloxy-$C_1$–$C_6$-alkyl, it being possible for the aromatic, pyridyl, or thienyl ring to be substituted by one or more of the following: $C_1$–$C_4$-alkyl, $C_1$–$C_2$-haloalkyl, $C_3$–$C_6$-cycloalkyl, $C_1$–$C_4$-alkoxy; $C_1$–$C_2$-haloalkoxy, halogen, aryl or aryloxy, $R^2$ and $R^3$ are identical or different and are hydrogen, $C_1$–$C_4$-alkyl, $C_1$–$C_2$-haloalkyl, $C_1$–$C_4$-alkoxy, $C_1$–$C_2$-haloalkoxy, halogen, cyano or nitro, $R^4$ is hydrogen, $C_1$–$C_6$-alkyl or aryl, it being possible for the aromatic ring to be substituted by one or more of the following: $C_1$–$C_4$-alkyl, $C_1$–$C_2$-haloalkyl, $C_1$–$C_4$-alkoxy, $C_1$–$C_2$-haloalkoxy, halogen, cyano or nitro, and x is CH or N.

3. A compound of the formula I as set forth in claim 1, where $R^1$ is ethyl, $R^2$ and $R^3$ are hydrogen, $R^4$ is methyl and X is CH, the oxime ether radical being in the 3-position on the phenyl radical.

4. A compound of the formula I as set forth in claim 1, where $R^1$ is ethyl, $R^2$ and $R^3$ are hydrogen, $R^4$ is methyl and X is N, the oxime ether radical being in the 3-position on the phenyl radical.

5. A compound of the formula I as set forth in claim 1, where $R^1$ is methyl, $R^2$, $R^3$ and $R^4$ are hydrogen and X is CH, the oxime ether radical being in the 3-position on the phenyl radical.

6. A compound of the formula I as set forth in claim 1, where $R^1$ is methyl, $R^2$, $R^3$ and $R^4$ are hydrogen and X is CH, the oxime ether radical being in the 4-position on the phenyl radical.

* * * * *